(12) United States Patent
Notaros et al.

(10) Patent No.: US 11,808,829 B2
(45) Date of Patent: *Nov. 7, 2023

(54) SLOTTED WAVEGUIDE ARRAY RF COIL FOR MAGNETIC RESONANCE SYSTEMS

(71) Applicant: Colorado State University Research Foundation, Fort Collins, CO (US)

(72) Inventors: Branislav Notaros, Fort Collins, CO (US); Milan Ilic, Belgrade (RS)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/694,907

(22) Filed: Mar. 15, 2022

(65) Prior Publication Data
US 2022/0206092 A1    Jun. 30, 2022

Related U.S. Application Data

(63) Continuation of application No. 16/753,841, filed as application No. PCT/US2018/054564 on Oct. 5, 2018, now Pat. No. 11,313,929.
(Continued)

(51) Int. Cl.
*G01R 33/36* (2006.01)
*G01R 33/34* (2006.01)
(Continued)

(52) U.S. Cl.
CPC .......... *G01R 33/3678* (2013.01); *A61B 5/055* (2013.01); *G01R 33/343* (2013.01);
(Continued)

(58) Field of Classification Search
CPC .......... G01R 33/3678; G01R 33/34092; G01R 33/343; G01R 33/345; G01R 33/365;
(Continued)

(56) References Cited

U.S. PATENT DOCUMENTS

| | | | |
|---|---|---|---|
| 2,807,018 | A | 9/1957 | Woodward |
| 5,138,261 | A | 8/1992 | Ratzel |

(Continued)

FOREIGN PATENT DOCUMENTS

DE    102011111996 B3  * 12/2012  ........... G01R 33/345

OTHER PUBLICATIONS

English translation of DE102011111996B3 provided by Espacenet. (Year: 2022).*
(Continued)

*Primary Examiner* — Rishi R Patel
(74) *Attorney, Agent, or Firm* — Meunier Carlin & Curfman LLC

(57) ABSTRACT

The exemplary system and method facilitate excitation of RF magnetic fields in ultra-high field (UHF) magnetic resonance (MRI) systems (e.g., MRI/NMR system) using a slotted waveguide array (SWGA) as an exciter coil. The exemplary exciter coil, in some embodiments, is configurable to provide RF magnetic field $B_1^+$ with high field-uniformity, with high efficiency, with excellent circular polarization, with negligible axial z-component, with arbitrary large field of view, and with exceptional possibilities for field-optimizations via RF shimming.

22 Claims, 29 Drawing Sheets

Related U.S. Application Data

(60) Provisional application No. 62/568,466, filed on Oct. 5, 2017.

(51) Int. Cl.
*G01R 33/343* (2006.01)
*G01R 33/345* (2006.01)
*A61B 5/055* (2006.01)
*G01R 33/38* (2006.01)
*G01R 33/561* (2006.01)

(52) U.S. Cl.
CPC ..... *G01R 33/345* (2013.01); *G01R 33/34092* (2013.01); *G01R 33/365* (2013.01); *G01R 33/3808* (2013.01); *G01R 33/5611* (2013.01)

(58) Field of Classification Search
CPC ............ G01R 33/3808; G01R 33/5611; G01R 33/3628; G01R 33/3415; A61B 5/055
See application file for complete search history.

(56) References Cited

U.S. PATENT DOCUMENTS

| | | | |
|---|---|---|---|
| 6,429,825 | B1 | 8/2002 | Martek |
| 11,313,929 | B2 * | 4/2022 | Notaros ............... G01R 33/343 |
| 2005/0062472 | A1 | 3/2005 | Bottomley |
| 2005/0264291 | A1 | 12/2005 | Vaughan et al. |
| 2008/0024133 | A1 | 1/2008 | Vaughan et al. |
| 2008/0180101 | A1 | 7/2008 | Bradshaw et al. |
| 2010/0253351 | A1 | 10/2010 | Huish et al. |
| 2012/0169340 | A1 | 7/2012 | Leussler et al. |
| 2013/0063145 | A1 | 3/2013 | Wiggins et al. |
| 2015/0323622 | A1 | 11/2015 | Wang |
| 2016/0124059 | A1 | 5/2016 | Notaros et al. |

OTHER PUBLICATIONS

International Search Report and Written Opinion dated Jan. 2, 2019, from International Application No. PCT/US2018/054564, 11 pages.
G. Adriany, P.-F. Van de Moortele, F. Wiesinger, S. Moeller, J. P. Strupp, P. Andersen et al., "Transmit and receive transmission line arrays for 7 Tesla parallel imaging," Magnetic Resonance in Medicine, vol. 53, pp. 434-445, 2005.
A. Andreychenko, et al., "Improved steering of the RF field of traveling wave MR with a multimode, coaxial waveguide," Magnetic Resonance in Medicine, vol. 71, pp. 1641-1649, 2013.
A. Andreychenko, et al., "Coaxial waveguide for travelling wave MRI at ultrahigh fields," Magnetic Resonance in Medicine, vol. 70, pp. 875-884, 2013.
D. O. Brunner et al., "Traveling-wave RF shimming and parallel MRI," Magnetic Resonance in Medicine, vol. 66, pp. 290-300, 2011.
H. P. Hetherington, N. I. Avdievich, A. M. Kuznetsov, and J. W. Pan, RF shimming for spectroscopic localization in the human brain at 7T, Magnetic Resonance in Medicine, vol. 63, pp. 9-19, 2010.
T. S. Ibrahim and L. Tang, "Insight into RF power requirements and B1 field homogeneity for human MRI via rigorous FDTD approach," Journal of Magnetic Resonance Imaging, vol. 25, pp. 1235-1247, 2007.
W. Mao, M. B. Smith, and C. M. Collins, "Exploring the limits of RF shimming for high-field MRI of the human head," Magnetic Resonance in Medicine, vol. 56, pp. 9 18-922, 2006.
C. J. Snyder et al., "Comparison between eight- and sixteen-channel TEM transceiver arrays for body imaging at 7 T," Magnetic Resonance in Medicine, vol. 67, pp. 954-964, 2012.
B. Zhang et al. "Whole body traveling wave magnetic resonance imaging at high field strength: Homogeneity, efficiency, and energy deposition as compared with traditional excitation mechanisms," Magnetic Resonance in Medicine, vol. 67, pp. 1183-1193, 2012.

* cited by examiner

SLOTTED WAVEGUIDE ARRAY RF COIL FOR MAGNETIC RESONANCE SYSTEMS

CROSS-REFERENCE TO RELATED APPLICATIONS

The present application is a continuation of U.S. patent application Ser. No. 16/753,841, filed on Apr. 6, 2020, which is a 371 National Phase entry of PCT App. No. PCT/US2018/054564, filed on Oct. 5, 2018, which claims priority to and the benefit of U.S. Provisional Patent App. No. 62/568,466, filed Oct. 5, 2017, all of which are incorporated by reference herein in their entireties.

GOVERNMENT SUPPORT CLAUSE

This invention was made with government support under ECCS-1307863 awarded by National Science Foundation. The government has certain rights in the invention.

BACKGROUND

Magnetic resonance imaging (MRI) is an established medical diagnostic method and tool widely utilized to obtain high-resolution images of the internal structure of the body or its parts and organs. The physical foundation of MRI is the principle of nuclear magnetic resonance (NMR), whereby atom nuclei of the tissue that is imaged absorb and reemit applied radio-frequency (RF) radiation based on the resonant radian frequency with which the spin precesses in an external polarizing static (dc) magnetic field (magnetic flux density), $B_0$, the Larmor frequency, $f_0$, that is proportional to $B_0$.

SUMMARY

The exemplary system and method facilitate excitation of RF magnetic fields in ultra-high field (UHF) magnetic resonance (MRI) systems (e.g., MRI/NMR system) (with main polarizing static magnetic field $B_0 > 3$ T) using a slotted waveguide array (SWGA) as an exciter coil. The exemplary exciter coil is configured to provide RF magnetic field $B_1^+$ with high field-uniformity. In some embodiments, the exemplary exciter coil is configured with high efficiency. In some embodiments, the exemplary exciter coil is configured with excellent circular polarization. In some embodiments, the exemplary exciter coil is configured with negligible axial z-component. In some embodiments, the exemplary exciter coil is configured with arbitrary large field of view. In some embodiments, the exemplary exciter coil is configured to provide exceptional possibilities for field-optimizations via RF shimming.

Each slotted waveguide antenna in the array is a mechanically robust structure capable of handling high powers. Each antenna is also a tuned resonator, with well-defined narrow-band operation, and almost perfectly decoupled from all other elements in the array. At the same time, each antenna can be easily detuned (e.g., for receiving operation). The exemplary method for RF excitation in MRI systems is universal and not limited to any particular UHF field strength and any particular frequency. SWGA coils can be used as body coils, head coils, limb coils, torso coils, partial body coils, etc. Potential applications include research, pre-clinical, and clinical MRI/NMR systems.

In an aspect, a magnetic-resonance (e.g., MRI or NMR) radio-frequency coil is disclosed. The MR radio-frequency coil comprises a plurality of slotted waveguides that collectively form an array circumferentially located around a longitudinal axis defining a bore scanning region of a magnetic resonance scanning system (e.g., MRI system or NMR system), wherein each of the plurality of slotted waveguide comprises an elongated body that extends along a pre-defined length, and parallel with, the longitudinal axis, and wherein each elongated body has an inner-facing surface, facing the longitudinal axis, that comprises a plurality of slots intermittently formed therein along a portion of the pre-defined length (e.g., so as to form a plurality of discrete tuned resonators at respective consecutive sections of the elongated body).

In some embodiments, the slots are formed across the inner-facing surface of the elongated body and extended inwardly to one or more side-surfaces of the elongated body adjoining the inner-facing surface.

In some embodiments, the slots (rectangular, parallelogram, circles, or any polygonal shapes) are formed only on the inner-facing surface of the elongated body.

In some embodiments, one or more of the plurality of slots of each elongated body is tilted at an angle (e.g., θ) from an axis, or an axis perpendicular thereto, extending along the pre-defined length of the elongated body.

In some embodiments, the elongated body of the plurality of slotted waveguide has, at non-slotted regions, an outer cross-sectional profile selected from the group consisting of a rectangle, a square, a circle, and an oval.

In some embodiments, each elongated body of the plurality of slotted waveguide forms a hollow tube (e.g., having wall sections defined by the outer-sectional profile). In some embodiments, a portion of the hollow tube is filled with a low-loss permittivity dielectric (e.g., to facilitate monomode $TE_{10}$ operation).

In some embodiments, the plurality of slotted waveguides terminates at a short-circuit element.

In some embodiments, the plurality of slotted waveguides terminates at a matched load element.

In some embodiments, each of the plurality of slots is intermittently formed at a location having a length of approximately $\lambda_g/2$ (e.g., for a standing wave antenna configuration) to a next slot, wherein $\lambda_g$ is a guided wavelength in the waveguide.

In some embodiments, a last slot is formed at a location having a length of approximately $\lambda_g/4$ (e.g., for a standing wave antenna configuration) to a short-circuit termination.

In some embodiments, the plurality of slotted waveguides have a number of slotted waveguides selected from the group consisting of 3, 4, 5, 6, 7, 8, 9, 10, 11, 12, 13, 14, 15, 16, 17, 18, 19, 20, 21, 22, 23, and 24.

In some embodiments, the MR radio-frequency coil further includes one or more dielectric lens (e.g., low-loss high-permittivity dielectric body) held in at least partial contact with, or in close proximity to, the inner surface of the elongated body of each of the plurality of slotted waveguides, or a portion thereof.

In some embodiments, the plurality of slotted waveguides is configured for 3 T magnetic field.

In some embodiments, the plurality of slotted waveguides is configured for 7 T magnetic field.

In some embodiments, the array is configured as one of the groups of a body coil, a head coil, a limb coil, and a torso coil.

In another aspect, a method is disclosed of magnetic resonance scanning. The method includes providing a magnet that creates a primary magnetic field within a bore of an MR scanning system along a longitudinal axis of the bore; driving a slotted antenna radio-frequency coil array comprising a plurality of slotted waveguides oriented along the bore with an RF signal to generate a circularly polarized RF magnetic field perpendicular to the longitudinal axis; detecting a response signal generated by tissues of a subject at least partially positioned in a volume defined by the slotted antenna radio-frequency coil in response to the circularly polarized RF magnetic field; and creating an image of the tissues of the subject based on the detected response signal.

In some embodiments, the slotted antenna radio-frequency coil array are driven by multichannel excitation sequence in which each of the excitation are highly decoupled among the channels.

In some embodiments, the slotted antenna radio-frequency coil array has a magnetic field maximum transmission efficiency of greater than 1.1 $\mu T/\sqrt{W}$ (e.g., at least 2.39 $\mu T/\sqrt{W}$).

In some embodiments, the circularly polarized RF magnetic field converges at a region in the bore having a high spatial uniformity of the transverse $B_1$-field along the longitudinal axis of the bore and a low axial $B_1$ field.

In another aspect, a magnetic resonance (MR) scanning system is disclosed comprising: a structure defining a bore within which a subject is to be positioned for scanning, the bore defining a longitudinal axis; a magnet to generate a primary magnetic field within the bore parallel to the longitudinal axis; an RF signal generator to drive the slotted-waveguide radio-frequency (RF) antennae coil to generate a circularly polarized (CP) RF magnetic field perpendicular to the longitudinal axis; an RF detector to detect a response signal generated by tissues of the subject in response to the CP RF magnetic field; a computing system to create an image of the tissues of the subject based on the detected response signal; and a slotted-waveguide radio-frequency (RF) antenna coil of any one of above claims, wherein the coil is oriented along the longitudinal axis to at least partially surround the subject when the subject is positioned within the bore for scanning.

BRIEF DESCRIPTION OF DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED SPECIFICATION

Each and every feature described herein, and each and every combination of two or more of such features, is included within the scope of the present invention provided that the features included in such a combination are not mutually inconsistent.

Figure 1:
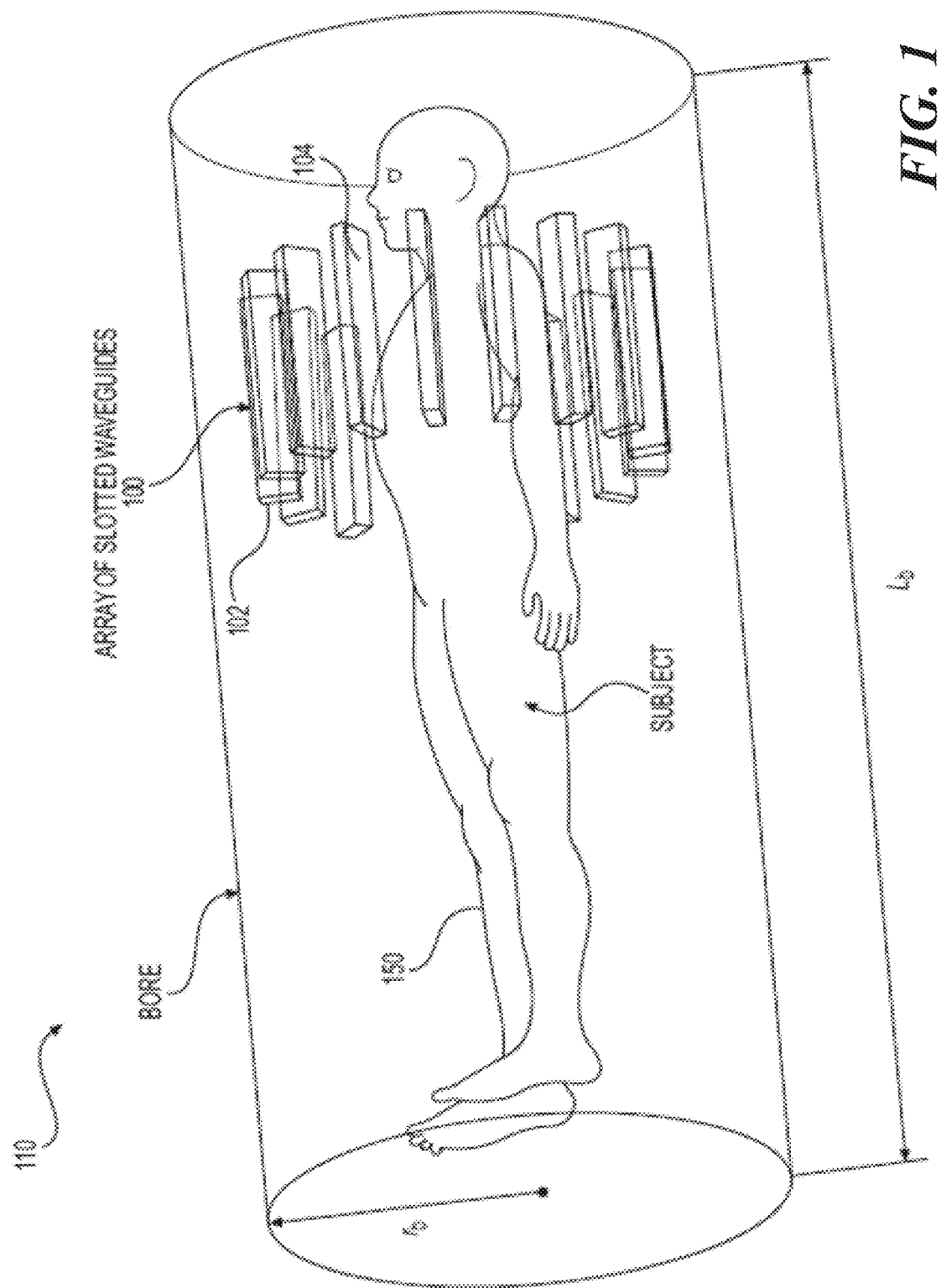
FIG. 1 shows an array of magnetic resonance radio-frequency coil configured with slotted waveguides, in accordance with an illustrative embodiment.

FIG. 1 shows an array 100 of magnetic resonance radio-frequency coil 102 (also referred to herein as a slotted waveguide antenna) configured with slotted waveguides 104, in accordance with an illustrative embodiment. Each of the magnetic resonance radio-frequency coil 102 includes a plurality of slotted waveguides 104 that collectively form the array 100. The array 100 is circumferentially located around a longitudinal axis 106 (also referred to herein as the z-axis, see FIG. 15) defining a bore scanning region 108 (not shown) of a magnetic resonance scanning system 110.

As used herein, magnetic resonance systems refer to magnetic resonance imaging system as well as nuclear magnetic resonance systems, including MRI and NMR systems at $B_0$ fields of 3 T, 4 T, 7 T, 9.4 T, 10.5 T, 11 T, 16.4 T, and 21.1 T.

This exemplary method and apparatus facilitate excitation of RF magnetic fields in ultra-high-field (UHF) magnetic resonance imaging (MRI) systems (with main polarizing static magnetic field $B_0>3$ T), using a slotted waveguide array (SWGA). The exciter ("coil") provides RF magnetic field $B_1$ with high field-uniformity, high efficiency, excellent circular polarization, negligible axial z-component, arbitrary large field of view, and exceptional possibilities for field-optimizations via RF shimming Each slotted waveguide antenna in the array is a mechanically robust structure capable of handling high powers. Each antenna is also a tuned resonator, with well-defined narrowband operation, and almost perfectly decoupled from all other elements in the array. At the same time, each antenna can be easily detuned (e.g., for receiving operation). The exemplary method for RF excitation in MRI systems is universal and not limited to any particular UHF field strength and any particular frequency. SWGA coils can be used as body coils, head coils, limb coils, torso coils, partial body coils, etc. Potential applications include research, pre-clinical, and clinical MRI/NMR systems.

Figure 2:
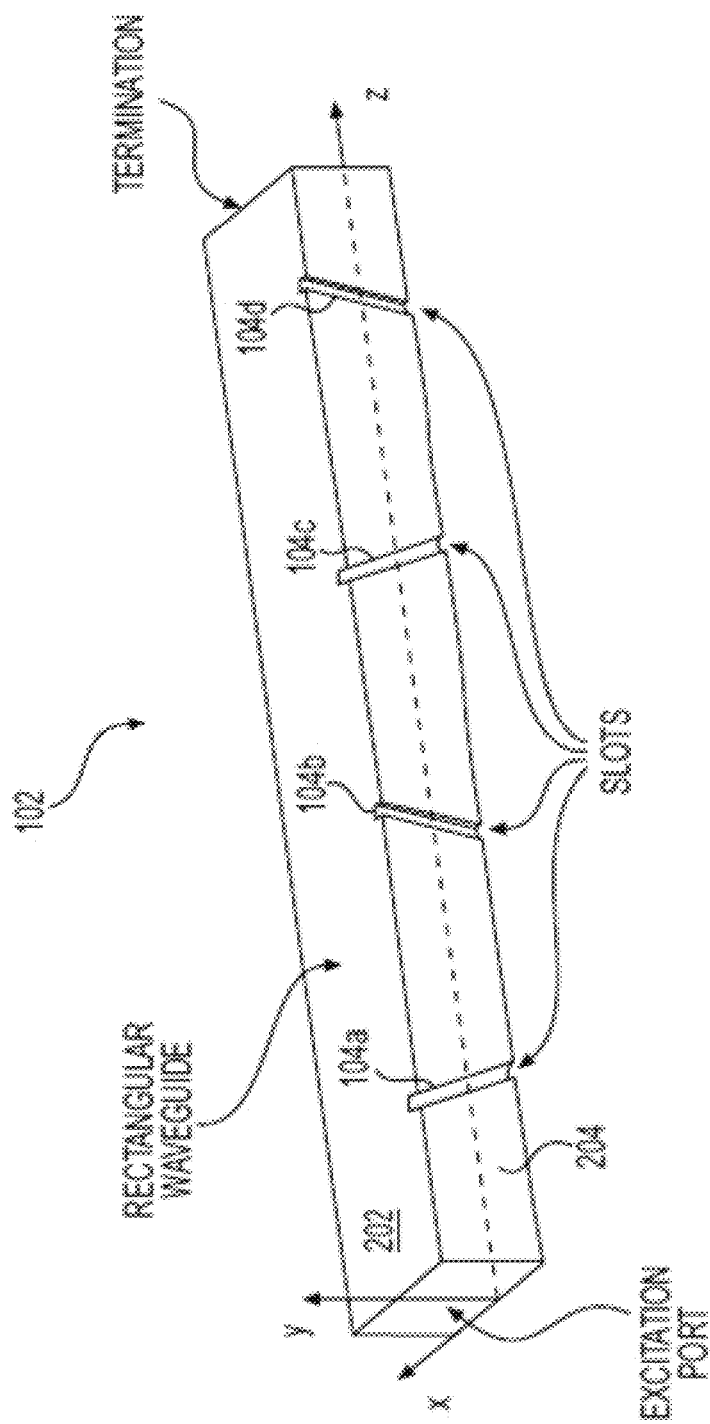
FIG. 2 shows a detail view of a magnetic resonance radio-frequency coil, in the array of FIG. 1, configured with the slotted waveguide, in accordance with an illustrative embodiment.

FIG. 2 shows a detail view of a magnetic resonance radio-frequency coil 102, in the array 100 of FIG. 1, configured with the slotted waveguide 104. The slotted waveguide 104 comprises an elongated body 202 that extends along a pre-defined length, and parallel with, the longitudinal axis 106. Each elongated body 202 has an inner-facing surface 204, facing the longitudinal axis, that comprises the plurality of slots 104 (shown as 104a, 104b, 104c, and 104d) intermittently formed therein along a portion of the pre-defined length so as to form a plurality of discrete tuned resonators at respective consecutive sections of the elongated body.

As shown in FIG. 2, the slots are formed across the inner-facing surface 204 of the elongated body 202 and extended inwardly to one or more side-surfaces of the elongated body adjoining the inner-facing surface.

As shown in FIG. 2, a single slotted waveguide antenna consists of a (e.g., rectangular) waveguide with slots milled into its conducting walls. Depending on the desired polarization, the slots can be milled on either the broad, or the narrow, waveguide wall. In either case, the slots introduce discontinuities in the metallic waveguide structure, thus interrupting the flow of (surface) electric current in the waveguide walls. As a result, the current has to flow around the slots, which, in turn, introduces radiation. Without wishing to bound to a particular theory, from the Babinet's principle point of view, each slot represents a dipole-like antenna (with polarization orthogonal to that of the dual electric dipole). Moreover, because the slots are milled periodically along the waveguide, with each slot 104 being fed by the wave inside the waveguide, the slotted waveguide antenna behaves like a linear uniform phased array of dipoles. To achieve desired polarization in the instant application, a slotted waveguide antenna with slots in the narrow wall is used. As shown in FIG. 2, the slotted waveguide 104 are formed on the narrow waveguide wall, i.e., on the inner-facing surface 204 of the elongated body 202.

There are two basic types of slotted waveguide antennas: a standing-wave antenna and a travelling-wave antenna. In both cases the antenna is fed at the excitation port and operates in the monomode ($TE_{10}$) regime. However, in a standing wave antenna, the waveguide is terminated with a short-circuit (metallic plate), whereas in a travelling wave antenna, the waveguide is terminated with a matched load (absorber). Standing wave slotted waveguide antennas, being a form of resonators, are inherently narrowband, but they are easier to manufacture than the traveling wave antennas. In addition, their narrow bandwidth can actually be a desired property in MR application, where RF excitation is required strictly at the Larmor frequency and the radiation in the broader spectrum is actually considered as a loss. Although travelling-wave antennas can also be used as RF exciters in MRI via use of a short-circuited slotted waveguide antennas.

In some embodiments, the waveguide is sealed and filled with a low-loss powder dielectric or a low-loss liquid dielectric. In some embodiments, the low-loss powder dielectric is suspended in a liquid or a solid filler.

Figure 3:
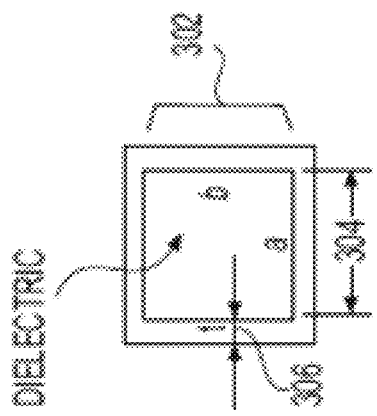
FIGS. 3 and 4 each show example geometric parameters of a slotted waveguide antenna, in accordance with an illustrative embodiment.
Figure 4:
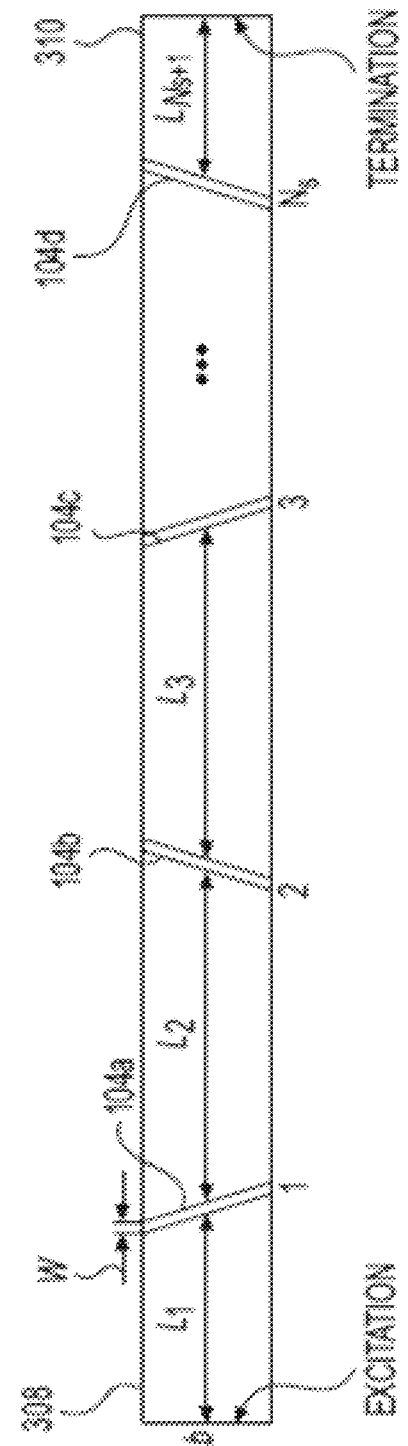

FIGS. 3 and 4 each show example geometric parameters of a slotted waveguide antenna (axial cross-sectional view, FIG. 3), in accordance with an illustrative embodiment. In FIG. 3, the inner width a (302) and the inner height b of the rectangular waveguide are shown in in which a>b, respectfully, with the wall thickness being t (306). In some embodiments, the wall thickness t is 17 mm or less (hence it is negligible for most purposes and thus it is most often not shown in the following figures), e.g., to minimize the induced eddy currents which may arise due to operation of the gradient coils. Of course, other wall thickness and cross-sectional profile can be used.

With reference to FIG. 4, where the waveguide narrow wall with slots is shown, the slots are numbered starting from the excitation port 308 on the left, towards the termination 310 on the right. The number of slots $N_s$ can be smaller or larger depending on the desired FOV. The distance between the excitation port (308) and the first slot (104a), $l_1$, distances among the slots, $l_2, l_3, \ldots, l_{Ns}$, and the distance between the last slot and the termination, $l_{Ns+1}$ can all be optimized for optimal radiation and impedance matching. For appropriate operation, the distances between the slots are, in some embodiments, approximately $\lambda_g/2$ and, for the standing wave array, the distance between the last slot and the short-circuited termination (e.g., short-circuit metallic wall) is about $\lambda_g/4$, where $\lambda g$ stands for the guided wavelength in the waveguide. Distance $l_1$ varies on the type of the waveguide feed, but it can be considered to be $\lambda_g/4$ as well. As shown in FIG. 2, the slotted waveguide antenna includes 4 slots milled into the narrow wall. The slotted waveguide antenna can have any number of slots including, but not limited to, 3, 4, 5, 6, 7, 8, 9, 10, 11, 12, 13, 14, 15, 16, 17, 18, 19, 20, 21, 22, 23, and 24.

Figure 5:
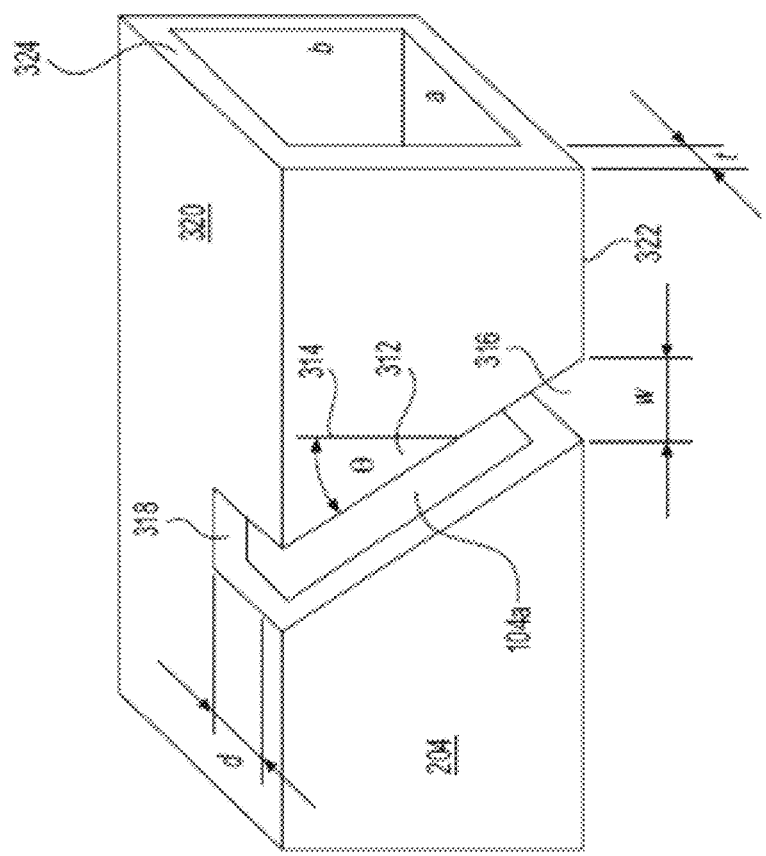
FIG. 5 is a detailed view of a single slot in the slotted waveguide of FIG. 4, in accordance with an illustrative embodiment.

FIG. 5 is a detailed view of a single slot 104a in the slotted waveguide 102 of FIG. 4, in accordance with an illustrative embodiment. The slot 104a is tilted at an angle θ (312) from the vertical axis (314) (e.g., to enable efficient disruption of the currents), its width is w (316), and its depth extending beyond the wall thickness is d (318). This geometry ensures efficient radiation, e.g., with a dipole-like behavior. The geometry, in particular, the angle θ (312) can be adjusted to produce optimal radiation.

Indeed, the slot waveguide 104 is defined by the gap w (316) that is formed across the inner-facing surface 204 tilted at an angle θ (312) and that extended inwardly by distance d (318) on to side-surfaces (320, 322) of the elongated body adjoining the inner-facing surface 204.

As shown in FIG. 5, the elongated body 202, in some embodiments, forms a hollow tube in which a non-slotted region 324 (i.e., a region defined without a slot waveguide) has an outer cross-sectional profile of a rectangle. Of course, the elongated body 202 can be formed with other outer cross-sectional profile such as, but not limited to, a square, a circle, or an oval.

To enable a monomode, $TE_{10}$ operation, of the waveguide, the RF coil 102 can be configured with cross sectional width that is about $\lambda/2$, in which $\lambda$ is the (unguided) wavelength in the medium occupying the waveguide. Further, the space inside a waveguide can be filled with low-loss high permittivity dielectric, e.g., to ensure a short enough guided wavelength (which can facilitate reduction of the waveguide size).

At very high frequencies, this wavelength is small and the dielectric in the waveguide can be air. However, in MRI applications at 7 T, where Larmor frequency is about f=300 MHz, this dimension is prohibitively large to enable practical waveguide design. However, the waveguide can be filled with a low-loss high permittivity dielectric. For instance, a dielectric of water-like properties with relative permittivity $\varepsilon_r$=81 and conductivity σ=0.0002 S/m reduces the waveguide dimensions $\sqrt{\varepsilon_r}$=9 times. In some embodiments, the dielectric is sealed in a housing encasing the waveguide. In this case, a WR284 waveguide (a=72.14 mm, b=34.04 mm) can be used. Alternatively, similar non-standard rectangular waveguide with other cross-sectional shapes and geometry can be readily designed.

In the given example, the RF coil 102 has $\lambda_0=c_0/f$=0.999308 m, where $\lambda_0$ and $c_0$ are the free-space wavelength and the speed of light in a vacuum, respectively, the parameter $\lambda$ can be expressed as $\lambda=\lambda_0/\sqrt{\varepsilon_r}$=0.111034 m. The cutoff frequency for the $TE_{10}$ mode is computed as $f_c$=c/(2a)=$c_0/(2a\sqrt{\varepsilon_r})$=230.872 MHz. The cutoff frequency for the $TM_{01}$ mode in this case is 489.281 MHz. This provides a monomode window of operation from 230.872 MHz to 489.281 MHz. Indeed, the guided wavelength in this case is $\lambda_g=\lambda/\sqrt{1-(f_c/f)^2}$=173.883 mm. At these operating conditions (allowing higher cutoff frequency of the dominant mode, i.e., closer to the operating frequency f), a dielectric of lower permittivity (most commonly associated with lower dielectric losses) can be used as a waveguide filler, while keeping the waveguide dimensions and other geometrical parameters the same.

Figure 6:
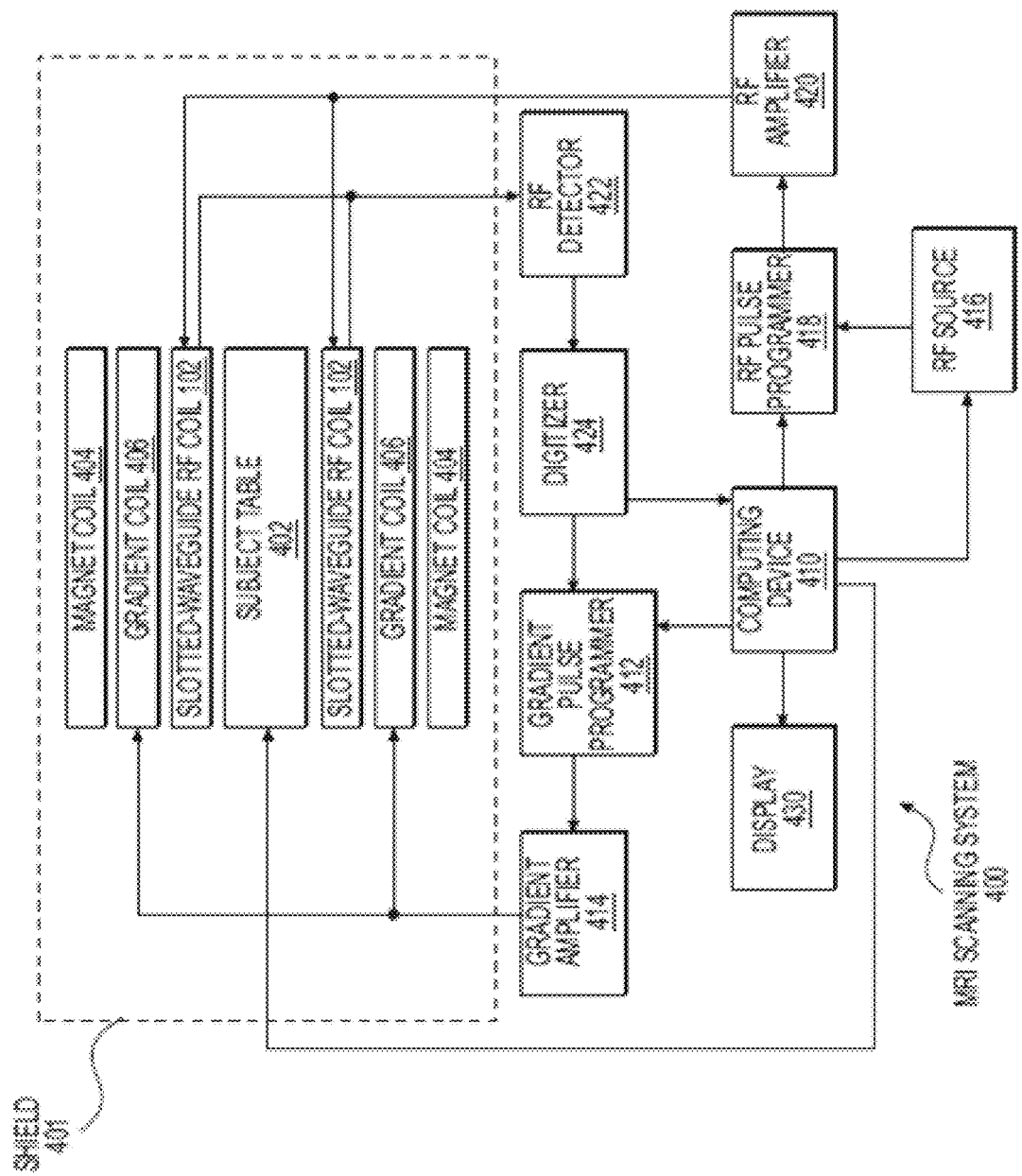
FIG. 6 is a block diagram of an example MRI scanning system configured with an array of slotted-waveguide-antenna RF coils of FIG. 1, in accordance with an illustrative embodiment.
Figure 7:
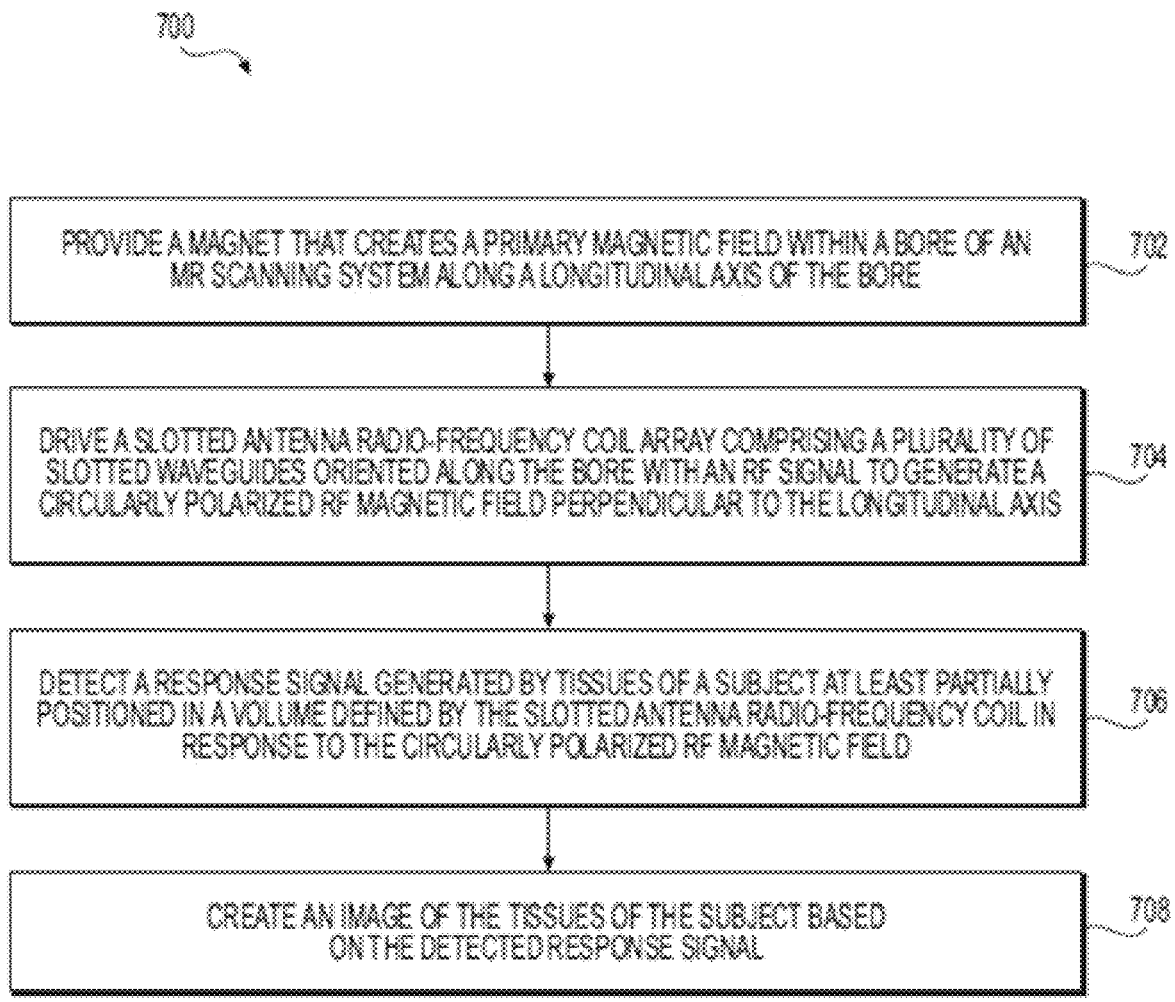
FIG. 7 is a method of operating the example MRI scanning system configured with an array of slotted-waveguide-antenna RF coils and is discussed concurrently with FIG. 6, in accordance with an illustrative embodiment.

FIG. 6 is a block diagram of an example MRI scanning system 400 configured with an array of slotted-waveguide-antenna RF coils 102 of FIG. 1. FIG. 7 is a method of operating the example MRI scanning system 400 configured with an array of slotted-waveguide-antenna RF coils 102 and is discussed concurrently with FIG. 6.

In some embodiments, the MRI scanning system 400 includes a magnet coil 404, one or more gradient coils 406, and an array of slotted-waveguide antenna RF coils 102 (shown in pseudo-cross section in FIG. 4 to orient the reader) located within a magnetic shield 401 to prevent the field generated by the magnet coil 404 from interfering with equipment external to the MRI scanning system 400. In addition, the room within which the MRI scanning system 400 may employ RF shielding to prevent distortion of the MRI images being generated. Also included within the bore (not explicitly illustrated in FIG. 4) of the MRI scanning system 400 may be a motorized subject table 402 upon which a patient or other subject 150 may be placed to locate the subject 150 within the bore 120 under the control of a computing device 410.

The magnet coil 404 may provide (step 702) the primary polarizing static magnetic field $B_0$ within the bore and aligned parallel to the longitudinal axis of the bore (e.g., in the z-direction). The one or more gradient coils 406 may be oriented to apply a magnetic field gradient to the primary magnetic field $B_0$ in the z-direction that vary the resonant frequency in space and time, in some embodiments, the gradient coils 406 applies the magnetic field gradient so that only a single virtual axial "slice" of the subject 150 being scanned is responsive to the transverse excitation field $B_1$ associated with a particular resonant frequency. In some examples, one or more shim coils may also be employed in the MRI scanning system 400 to alleviate inhomogeneities in the primary magnetic field $B_0$ generated by the magnet coil 404.

Also, one or more of the gradient coils 406 may be employed to create gradients in the x-direction and y-direction (e.g., transverse to the z-direction) of the primary magnetic field $B_0$ so that a small portion of the selected axial slice of the subject 150 may generate a relaxation response to the transverse excitation field $B_1$ generated by a particular RF excitation signal frequency. The computing device 410 may program or control a gradient pulse programmer 412 to generate pulsed signals that are subsequently amplified by a gradient amplifier 414 and used to drive the gradient coils 406 to alter the primary magnetic field $B_0$ as described above. In addition, an insert gradient coil (not illustrated in FIG. 6), sometimes installed within the bore 120 to enhance the performance of the MRI scanning system 400, may be employed in conjunction with the slotted-waveguide antenna RF coil 102.

The slotted-waveguide antenna RF coil 102 can generate (step 704) the RF signal and associated transverse magnetic field $B_1$ employed to excite the subject 150 tissue for imaging purposes. To that end, the computing system 410 may control an RF source 416 that may generate one or more RF excitation voltages, as well as an RF pulse programmer 418 that produces pulses of the RF excitation voltages received from the RF source 416. The resulting RF pulse signals may then be amplified by way of an RF amplifier 420 and forwarded to the slotted-waveguide-antenna RF coil 102. Indeed, the slotted-waveguide-antenna RF coil 102 can apply an RF excitation magnetic field $B_1$ in orthogonal direction to the main polarizing field, so in the transversal directions with respect to the MRI bore axis, to alter alignment of spins and induce an echo signal that is used in MRI. For maximum coupling between the RF field and the spins in the tissue, a rotating magnetic field with constant magnitude during rotation is desired, that is, the RF exciter needs to generate a circularly polarized (CP), and more precisely, right-hand CP (RCP) RF magnetic field, usually denoted as $B_1^+$.

The MRI scanning system 400, in some embodiments, also includes an RF detector 422 configured to detect (step 706) RF response signals generated by tissues of the subject 150 in response to the transverse magnetic field $B_1$. As shown in FIG. 4, the RF detector receives the response signals from the slotted-waveguide antenna RF coil 102; however, in other examples, a separate detection coil may be used for such a purpose. A digitizer 424 may digitize the RF signals detected at the RF detector 422 and provide the digitized signals to the computing device 410. In turn, the computing device 410 may employ the magnitude and other characteristics of the digitized signals to generate (step 708) images of the tissues of the subject 150, which may be presented by way of a display 430, as well as be stored in a data storage device or system (not explicitly depicted in FIG. 6).

In various embodiments of the MRI scanning system 400, the computing device 410 may include one or more processors that execute instructions that cause the computing device 410 to perform its various functions, as described above.

The MRI scanning system 400 represents just one particular example of an MRI/NMR system in which a slotted-waveguide-antenna RF coil may be employed, as many other types of scanning systems may use such a coil in various embodiments.

Table 1 gives Larmor frequencies for the currently available clinical, pre-clinical, and research MRI/NMR systems at $B_0$ fields of 3 T, 4 T, 7 T, 9.4 T, 10.5 T, 11 T, 16.4 T, and 21.1 T, respectively. MRI bores at 3 T and 7 T are typically 60 cm in diameter, allowing full-body human subjects, while 9.4 T and 21.1 T scanners are generally of smaller diameters (e.g., between about 30 cm and 10 cm) for use with phantoms and animals as subjects. A phantom is a container of an arbitrary shape, e.g., a cylindrical bottle, that is filled with a fluid resembling relative permittivity (dielectric constant) and conductivity parameters of human tissues and has NMR active species such as hydrogen molecules, e.g., saline water and deionized (DI) water. While the terminology largely varies, ultra-high field (UHF) magnetic resonance scanners are usually referring to the main polarizing static magnetic field values of $B_0 > 3$ T (i.e., Larmor frequency $f_0 > 127.8$ MHz).

TABLE 1

| Magnet $B_0$ | Larmor $f_0$ |
| --- | --- |
| 3T | 127.8 MHz |
| 4T | 170 MHz |
| 7T | 300 MHz |

TABLE 1-continued

| Magnet $B_0$ | Larmor $f_0$ |
| --- | --- |
| 9.4T | 400 MHz |
| 10.5T | 450 MHz |
| 11T | 468 MHz |
| 16.4T | 685 MHz |
| 21.1T | 900 MHz |

Dielectric Lens

Figure 8:
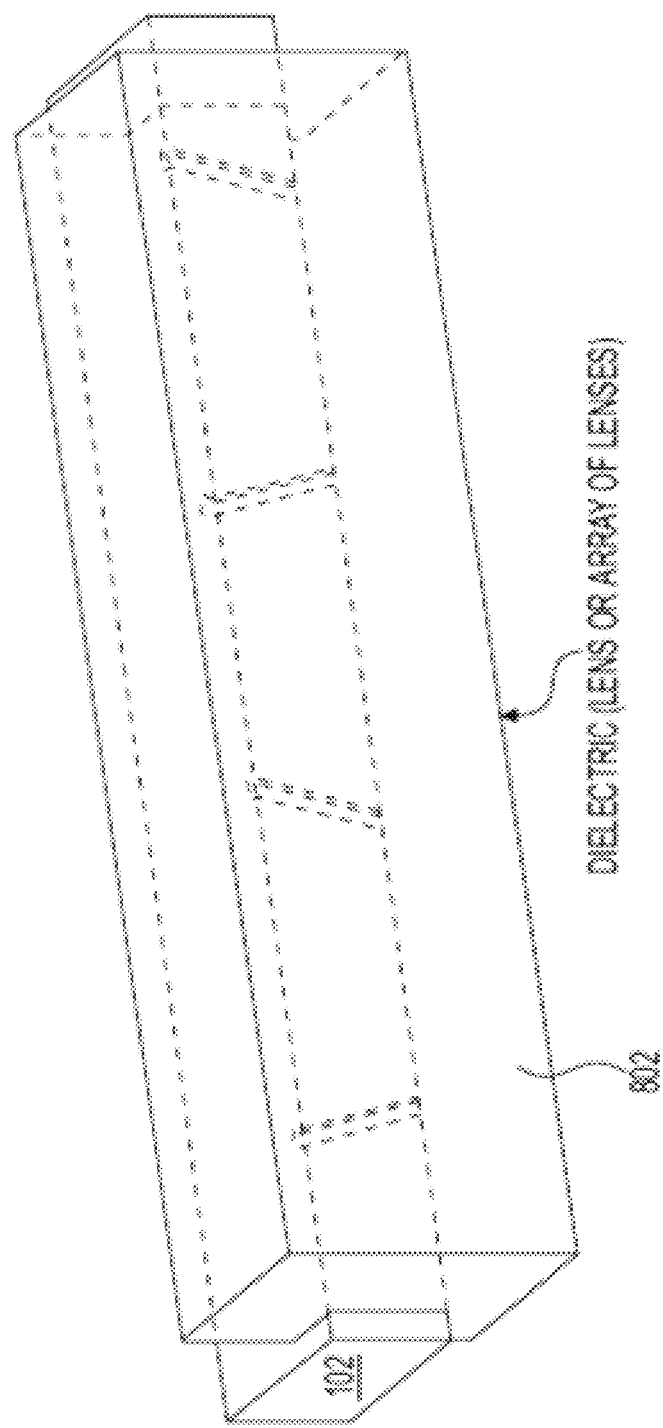
FIG. 8 shows a slotted waveguide RF coil configured with low-loss high-permittivity dielectric lens, in accordance with an illustrative embodiment.

To further improve the efficiency of the exciter, in some embodiments, the system includes a low-loss high-permittivity dielectric on each of the slotted waveguides. FIG. 8 shows a slotted waveguide RF coil 102 configured with low-loss high-permittivity dielectric 802 mounted on each of the slotted waveguides, e.g., in front and surrounding the slotted waveguide side. The dielectric 802 smooths the impedance transition from slots into free space and reduce the backward radiation. In a sense, the dielectric 802 performs as a basic lens and facilitates focusing of the radiation in the desired direction. Alternatively, a lens of optimized shape and dielectric profile, or array of lenses, can be utilized as well.

Feeding Structure

Figure 9:
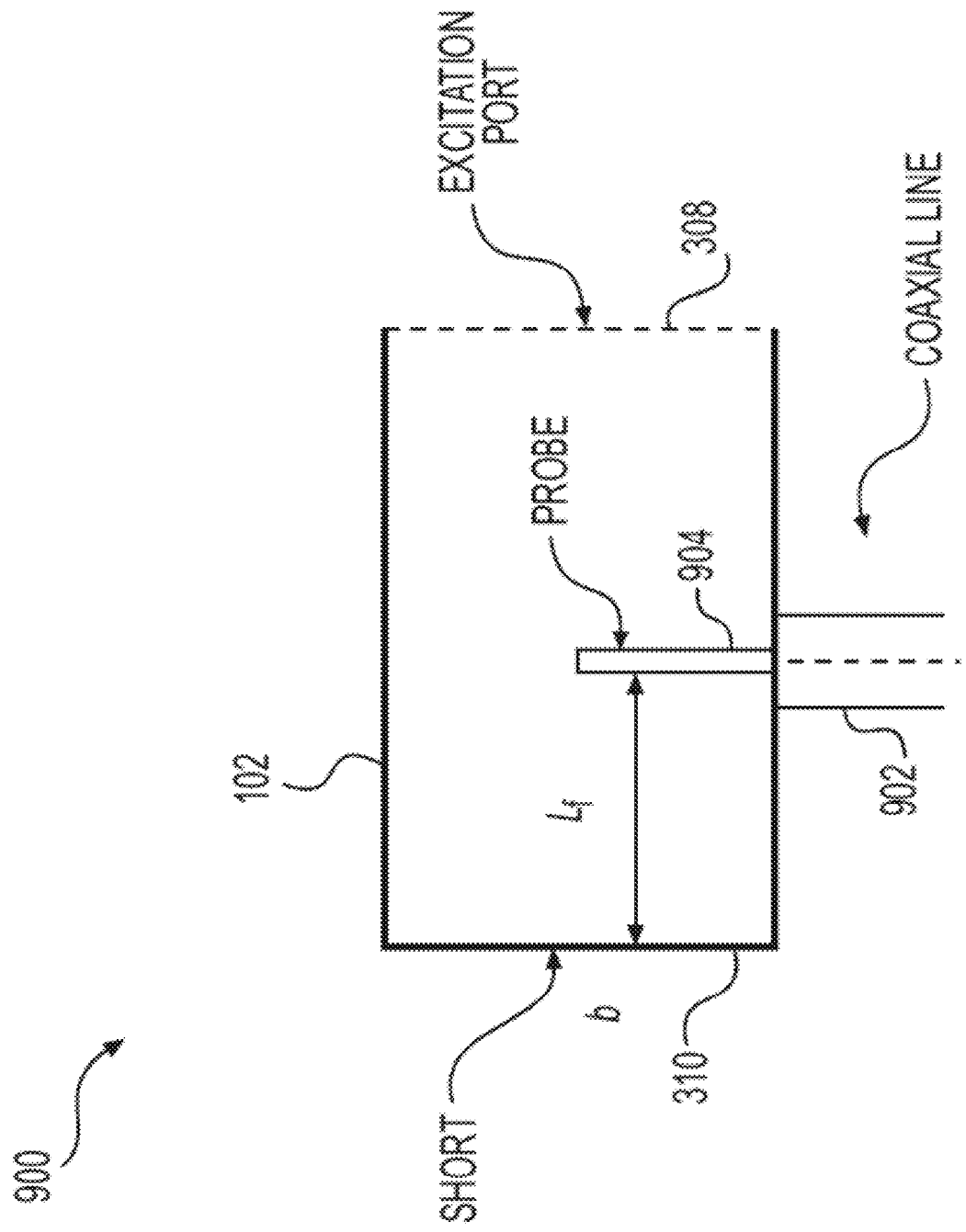
FIG. 9 shows an example feeding structure for the array of FIG. 1, in accordance with an illustrative embodiment.

FIG. 9 shows an example feeding structure 900 for the array 100 of FIG. 1, in accordance with an illustrative embodiment. In some embodiments, the feeding structure 900 includes a coaxial-line-to-rectangular-waveguide transition is used. In the array 100, each of the waveguides 102 is fed by a coaxial line 902 with a small probe 904 protruding into the rectangular waveguide 102. The probe 904 is located approximately $l_f \approx \lambda_g/4$ from the short-circuited termination 310. The height, diameter, and position of the probe 904 can be optimized to obtain (as close as possible) desired feeding parameters (e.g., input impedance) and for optimal excitation of the dominant $TE_{10}$ mode. To simplify field analysis, the feeding probe 904 is omitted in the models to follow and the waveguides are excited utilizing a standard $TE_{10}$ mode excitation via a wave-port, i.e., the excitation port 308 in FIG. 9 coincides with that in FIG. 4.

Other Embodiments of the Slotted Waveguide

In addition to angled slots, other slotted topologies may be used in the slotted-waveguide RF antenna coil 102.

As noted above, the elongated body of the plurality of slotted waveguide has, in some embodiments, at non-slotted regions, an outer cross-sectional profile selected from the group consisting of a rectangle, a square, a circle, and an oval.

Figure 10:
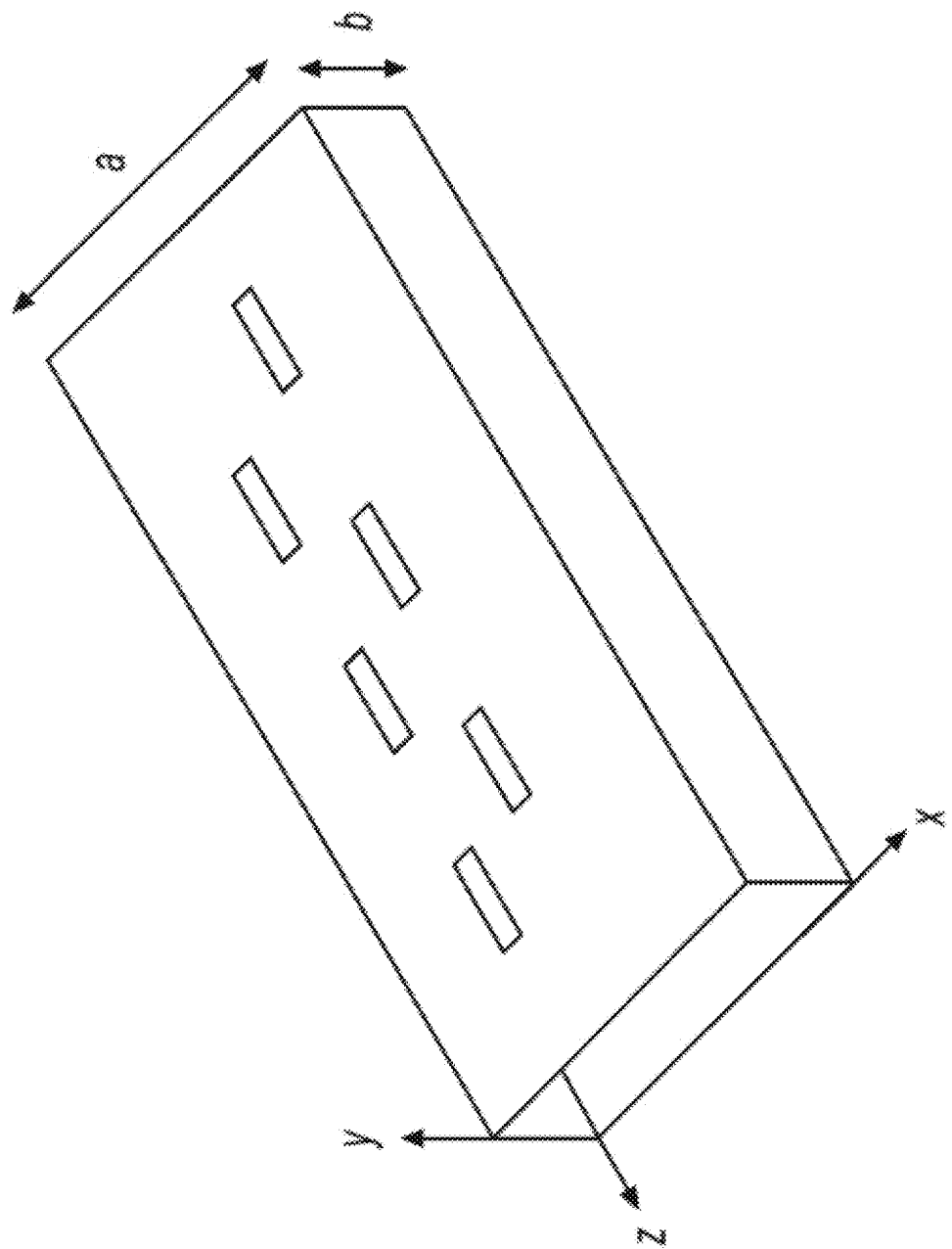
FIGS. 10-12 each shows embodiments of the slotted waveguide, in accordance with other illustrative embodiments.
Figure 11:
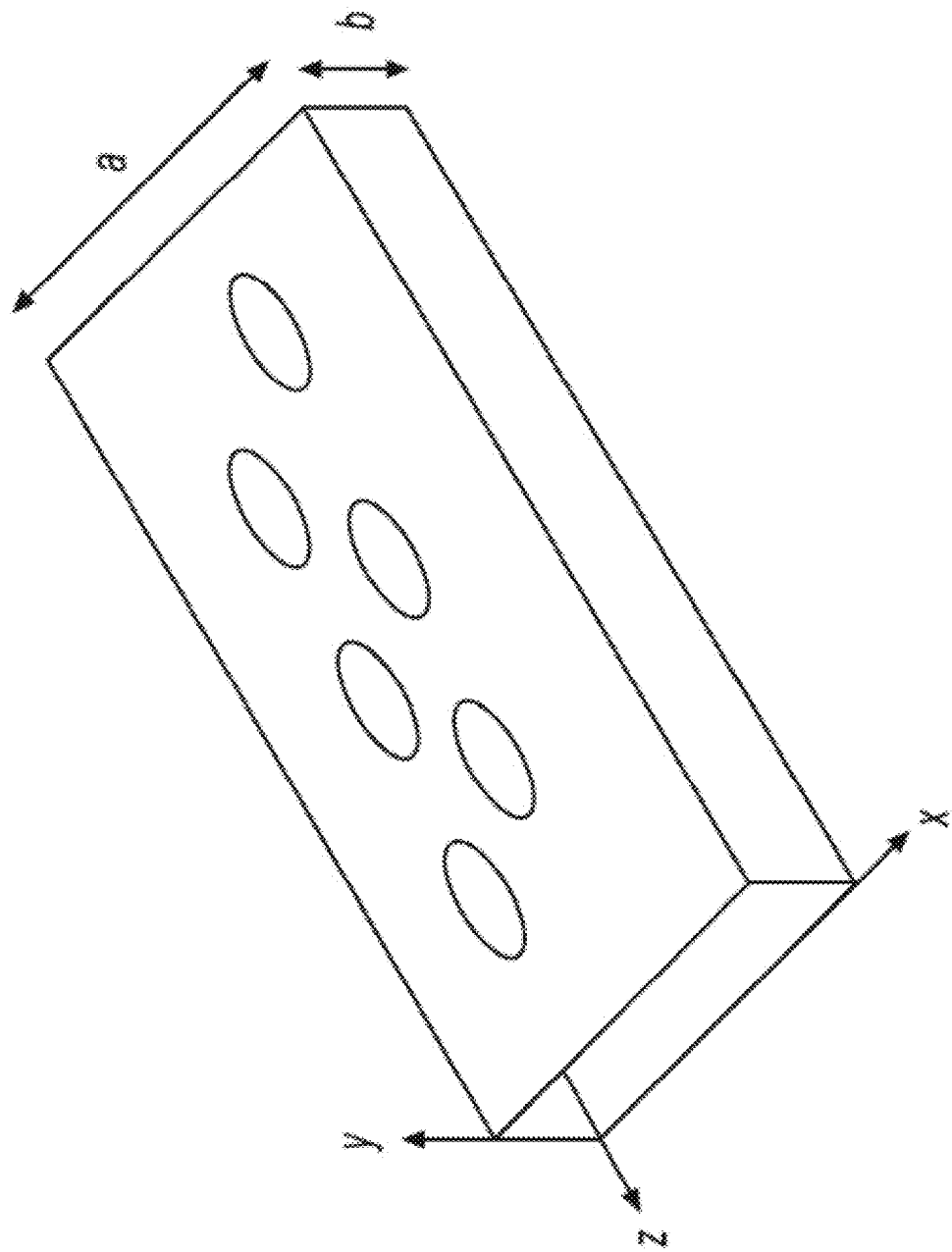
Figure 12:
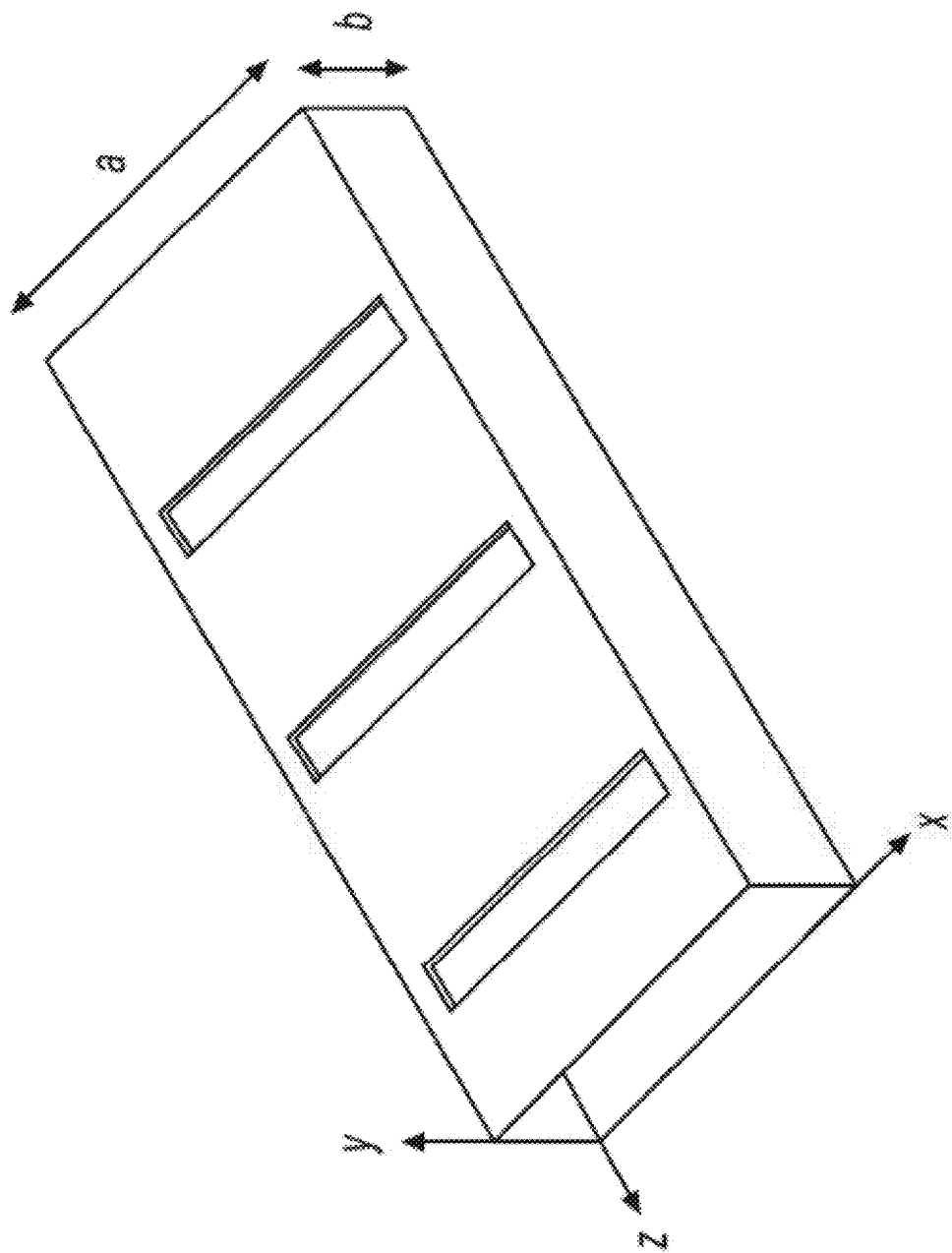

As shown in FIGS. 10-12, the slotted waveguide 104 can be formed having other shapes, e.g., rectangular, parallelogram, circles, or any polygonal shapes.

In case of travelling wave antennas, the distances between slots in the slotted waveguide may be non-uniform. In some embodiments, the slots are configured to be tapered towards the end.

Experimental Results

To examine the SWGA operation in a MR application, a study was conducted based on the geometric parameters of a slotted-waveguide RF coil 102 as shown in FIGS. 2-5, which include a number of slots $N_s=4$; $l_1=53.6338$ mm; $l_s=\lambda/4=43.4708$ mm; $l_2=l_3=l_4=\lambda/2=86.9416$ mm, $\theta=15°$, and $t=4$ mm.

Figure 13:
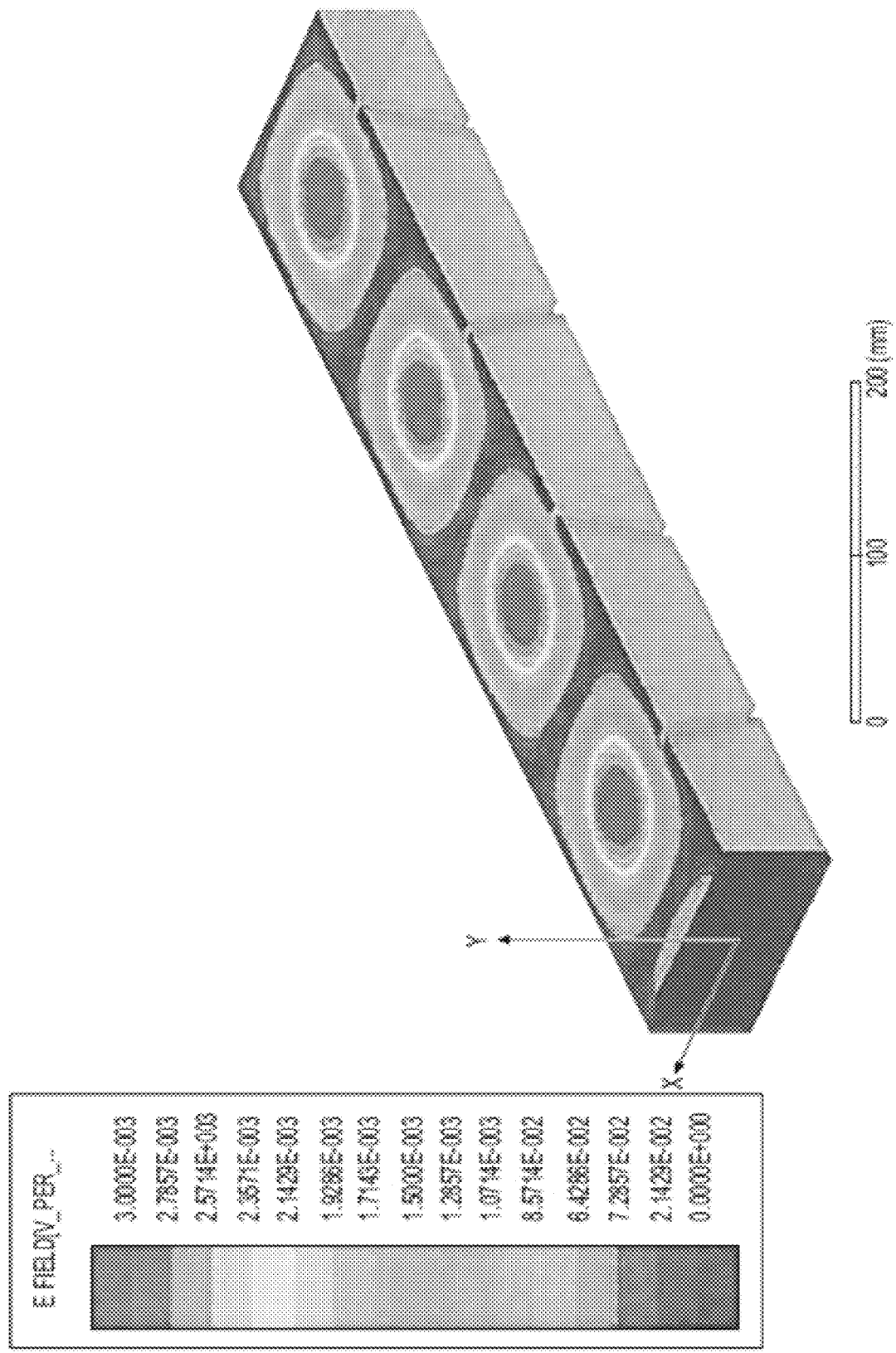
FIG. 13 shows simulation results of generated E-field in the waveguide from a single slotted waveguide, in accordance with an illustrative embodiment.

FIG. 13 shows simulated results of generated E-field in the waveguide from a single slotted waveguide, in accordance with other illustrative embodiments. Specifically, FIG. 13 shows the generated E-field (complex magnitude) in the waveguide from a single slotted waveguide (with the parameters given in FIGS. 2-5) in free space, for a 1 Watt incident power. It is clear from the FIG. 13 that the slots reside in areas where the standing wave in the waveguide has its maxima; this ensures optimal radiation.

Figure 14:
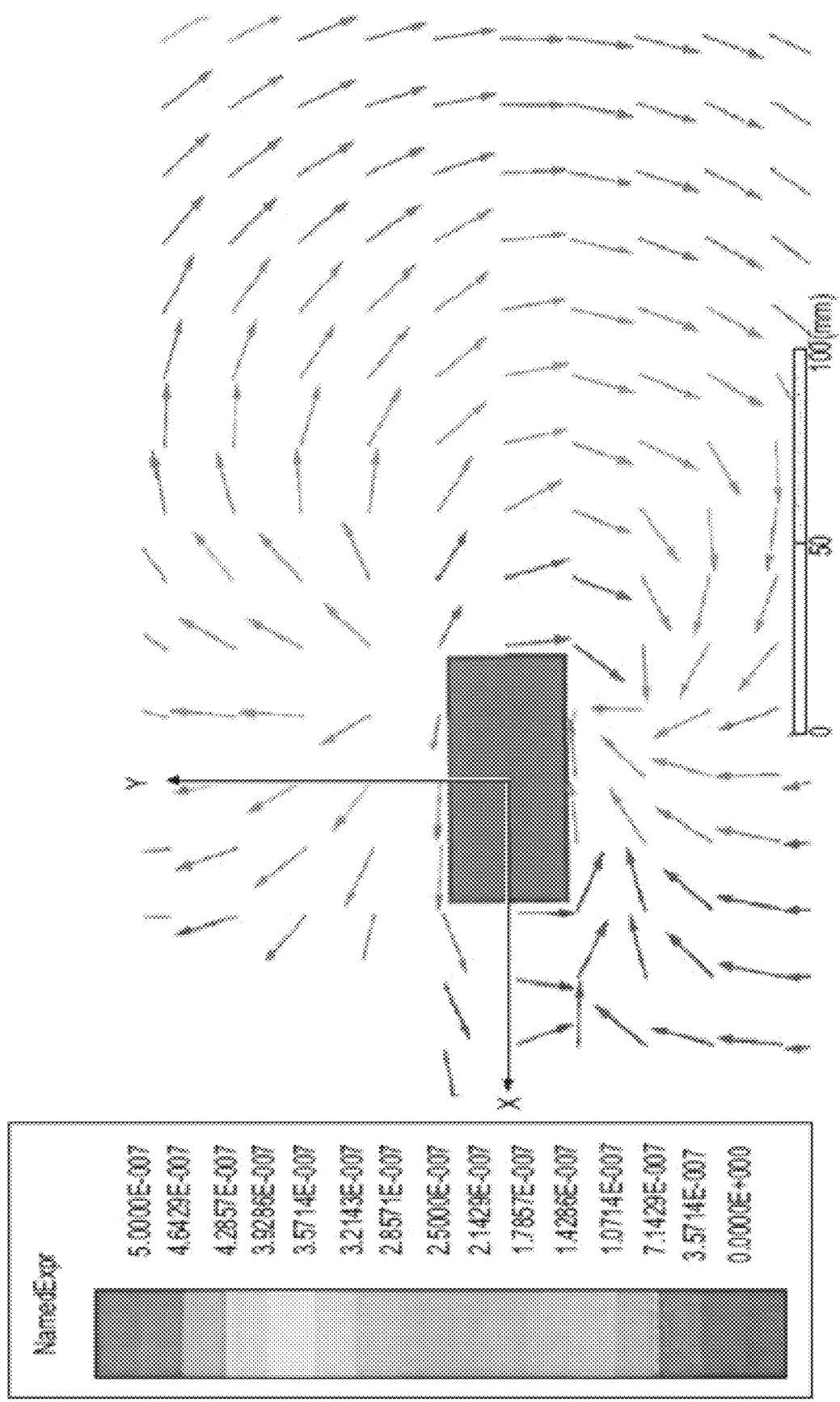
FIG. 14 shows simulation results of a vector plot of the instantaneous H-field generated by a single slotted waveguide, in accordance with an illustrative embodiment.

FIG. 14 shows simulation results of a vector plot of the instantaneous H-field generated by a single slotted waveguide, in accordance with an illustrative embodiment. Specifically, FIG. 14 shows vector plot of the instantaneous H-field in a plane perpendicular to waveguide z-axis, located in its middle. It can be seen from the figure that the antenna has a well-defined linearly polarized magnetic field oriented parallel to the waveguide narrow side (in the x-z plane). Further examination shows that at distances of a/2 from the slotted side, z-component of magnetic field practically vanishes. Moreover, the transverse field strength is very uniform along the z-axis of the antenna making it an excellent choice for MRI applications.

Figure 15:
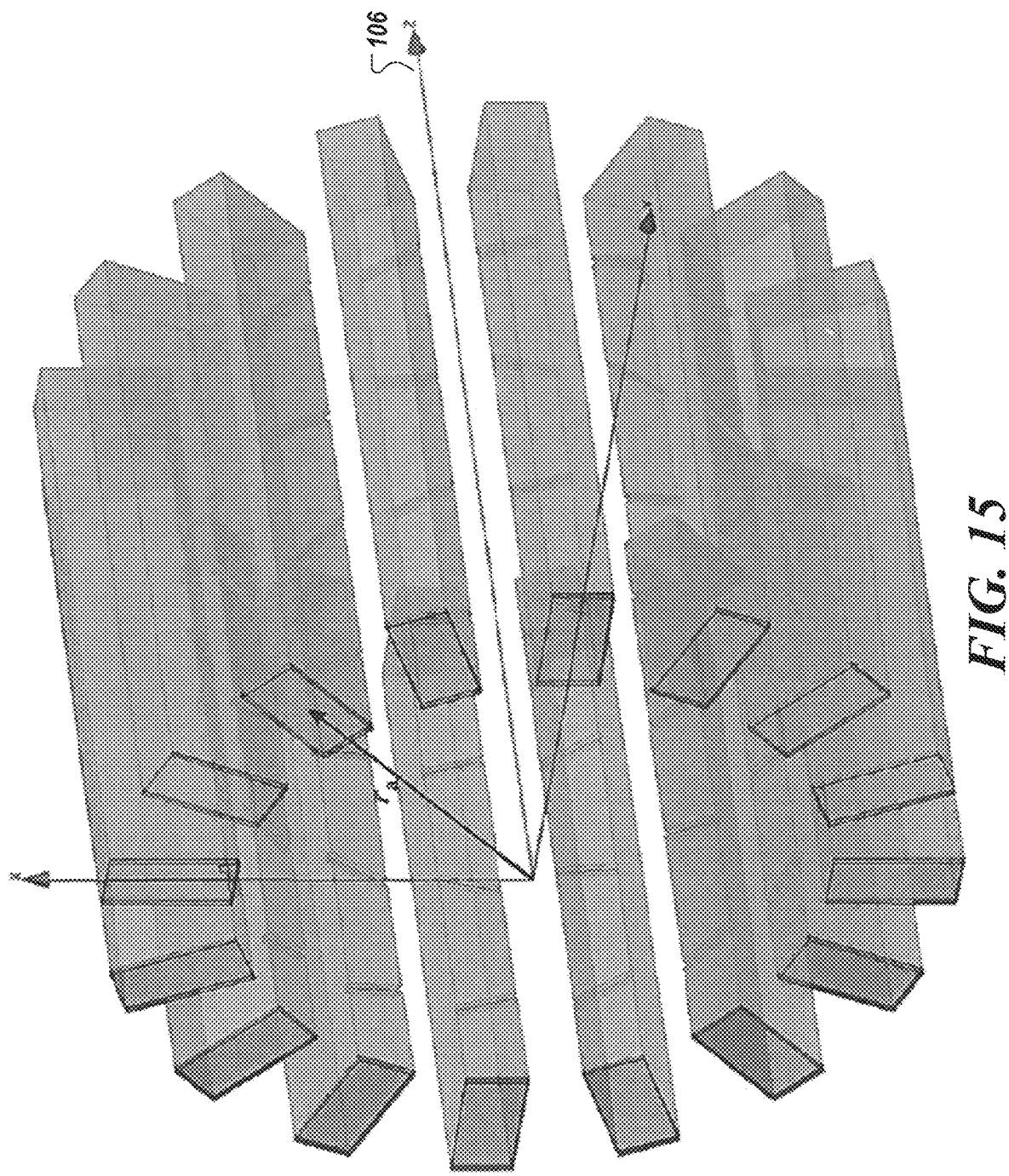
FIG. 15 shows an exemplary slotted waveguide array (SWGA) RF coil used in a study, in accordance with an illustrative embodiment.

To examine the SWGA operation in an MRI bore, another study was conducted to consider a metallic bore (shield) of radius $r_b$=450 mm and length $l_b$=1 m, placed coaxially with the array axis, with array centered in the bore. FIG. 15 shows an exemplary slotted waveguide array (SWGA) RF coil used in a study, in accordance with an illustrative embodiment. The study uses a number of coil $N_a$=16, and set the radius of the array (distance from the z-axis to the middle of the waveguide cross section, as shown in FIG. 5) to $r_a$=200 mm. The study excites each port with a "standard" excitation, i.e., equal incident power at all ports and phase shifts of $-2\pi/16$ between the excitations of adjacent elements in the clockwise direction, the study analyzed the magnetic field inside the unloaded array. To enable $TE_{10}$ excitation via wave-type ports, the waveguides were terminated at the ports (left side of array in FIG. 15) with metallic plugs $t_p$=3 mm thick. With dimensions of the slots and their distances given in FIG. 15, the total length of the waveguides is $l_w$=360 mm. The results of the analysis are shown in FIGS. 16A-F.

The study employs mathematical modeling, simulation, and analysis of MRI structures with novel RF exciters using full-wave numerical electromagnetic techniques that account for the geometry and material composition of the structure as is and include all high-frequency, far-field effects, as well as all low-frequency, near-field effects, by numerically exactly solving the underlying Maxwell's equations and associated field boundary conditions at any frequency. This is in contrast to approaches based on quasi-static approximations for the fields or those using analytical formulas and derivations, as well as numerical solutions, valid for simplified geometries intended to approximate the actual MRI structure under consideration.

Specifically, modeling and analysis of the MRI structures in the study is performed using a full-wave numerically rigorous computational electromagnetics (CEM) technique based on the method of moments (MoM) in conjunction with the surface integral equation (SIE) approach, implemented in a numerically higher order fashion. In this technique, all material (metallic and dielectric) surfaces in the structure are modeled using generalized parametric quadrilateral patches and all metallic wires are modeled by means of straight wire segments, electric and magnetic equivalent surface currents over elements (quadrilateral patches and wire segments) are modeled by polynomial vector basis functions, and SIEs based on boundary conditions for electric and magnetic field vectors are solved employing Galerkin method. In addition, the results obtained by the higher order MoM-SIE technique are thoroughly verified and validated by comparison with results using two well-established commercial full wave CEM codes, a finite element method (FEM) code ANSYS HFSS and a MoM code WIPL-D. The results shown in this document are those obtained by ANSYS HFSS.

Figure 16A:
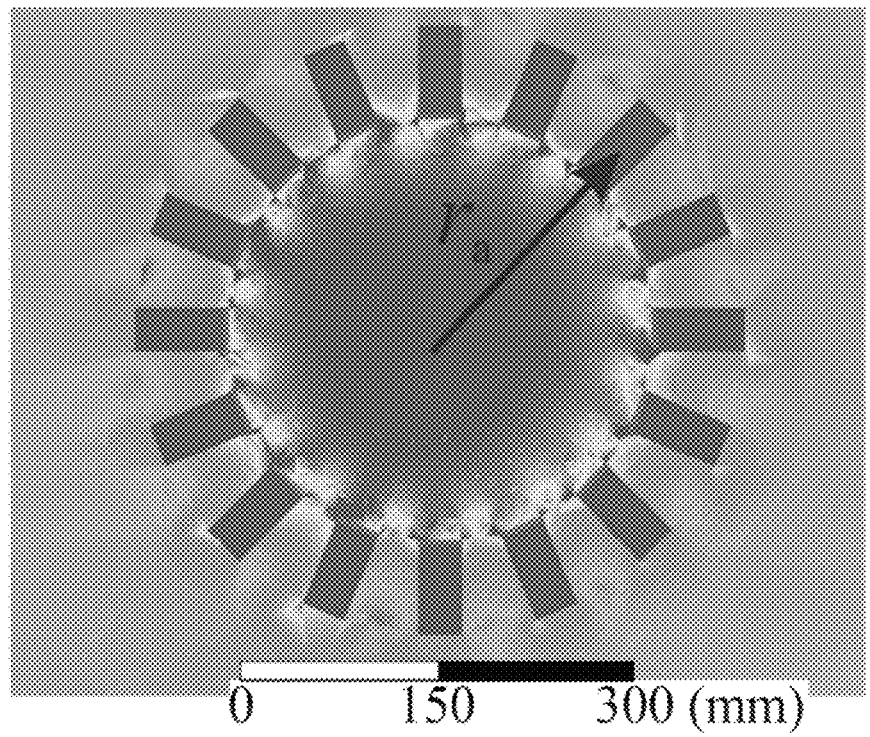
FIGS. 16A, 16B, and 16C show the right-hand circularly polarized component (FIG. 16A), the left-hand circularly polarized components (FIG. 16B), and z-component (FIG. 16C) of the simulated magnetic field transmit efficiency (in $T/\sqrt{W}$) in an axial cross-section of the SWGA RF coil of FIG. 15, in accordance with an illustrative embodiment.
Figure 16A:
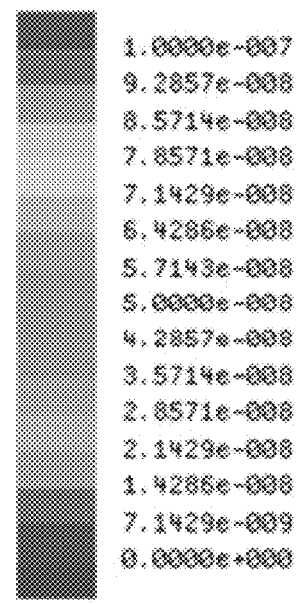
Figure 16B:
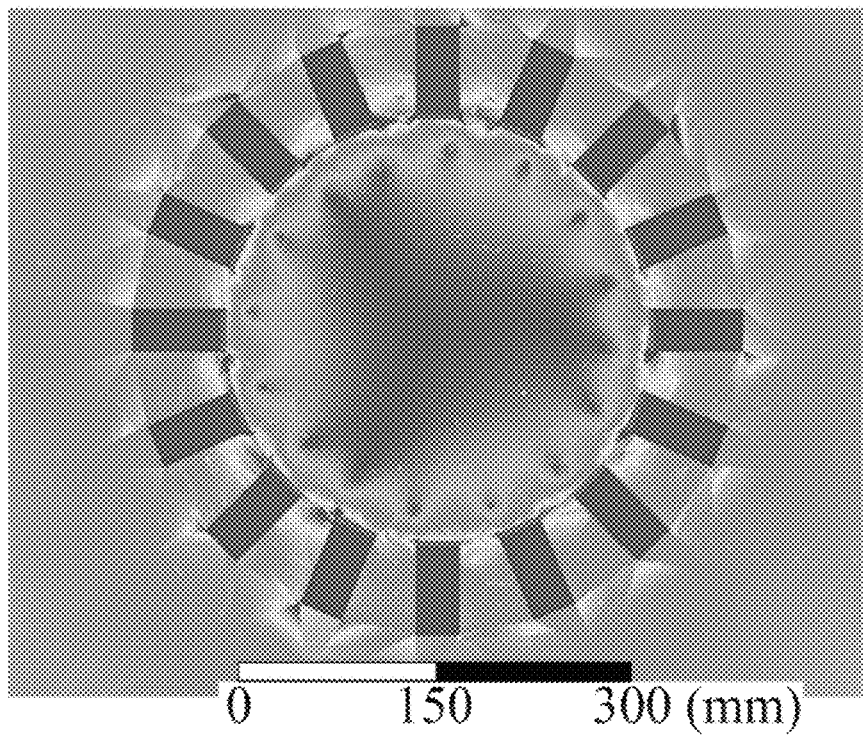
Figure 16B:
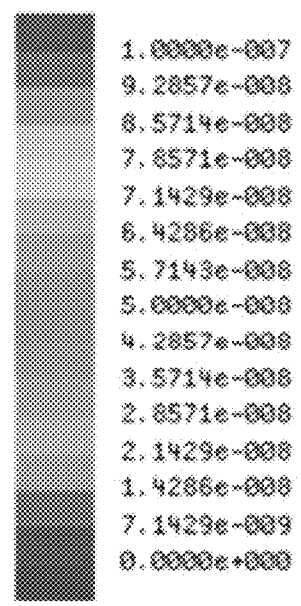
Figure 16C:
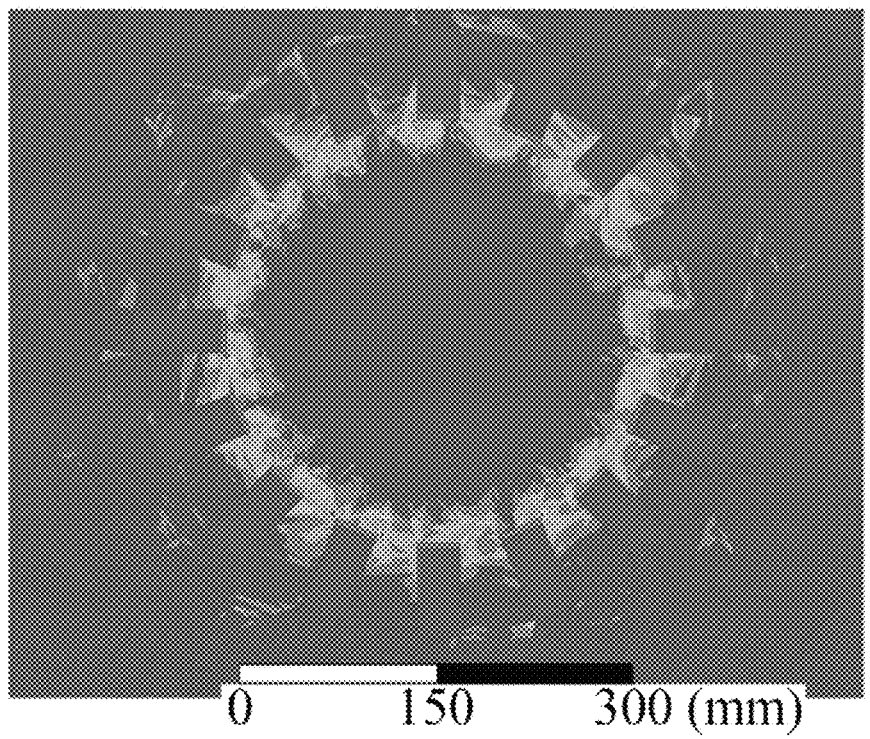

FIGS. 16A-16C show simulated complex magnitudes of the magnetic field components results of the SWGA RF coil of FIG. 15, in accordance with an illustrative embodiment. Specifically, FIGS. 16A-16C, respectively, show simulation of the right-hand circularly polarized component (FIG. 16A), the left-hand circularly polarized components (FIG. 16B), and z-component (FIG. 16C) of the magnetic field transmit efficiency (in $T/\sqrt{W}$) in an axial cross-section. The study concluded, as shown in the figures, that the array produces highly homogeneous $B_1^+$, extremely low $B_1^-$ (left-hand CP transverse field), and practically vanishing $B_z$ (axial component of B) in the whole region encompassed by the array (except in the region very close to the antennas, which is irrelevant for imaging applications). Indeed, the figures show that the favorable, RHCP, i.e., $B_1^+$, component of the field is dominantly generated, whereas the unwanted, LHCP and z-components, are practically negligible.

Figure 16D:
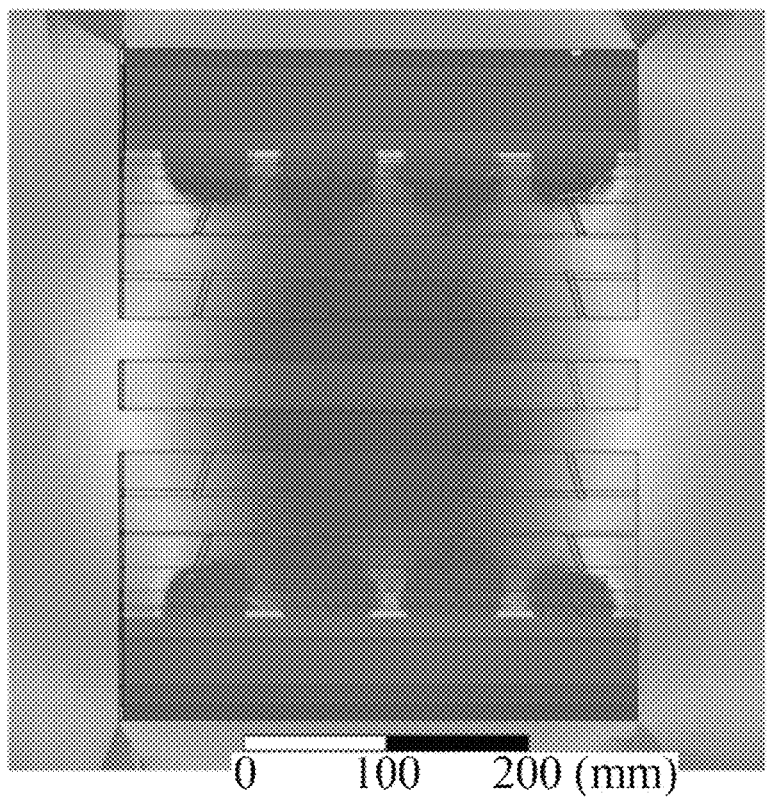
FIGS. 16D, 16E, and 16F show the complex magnitudes the magnetic field components (in T) generated of FIGS. 16A-16C in the sagittal cross section.
Figure 16E:
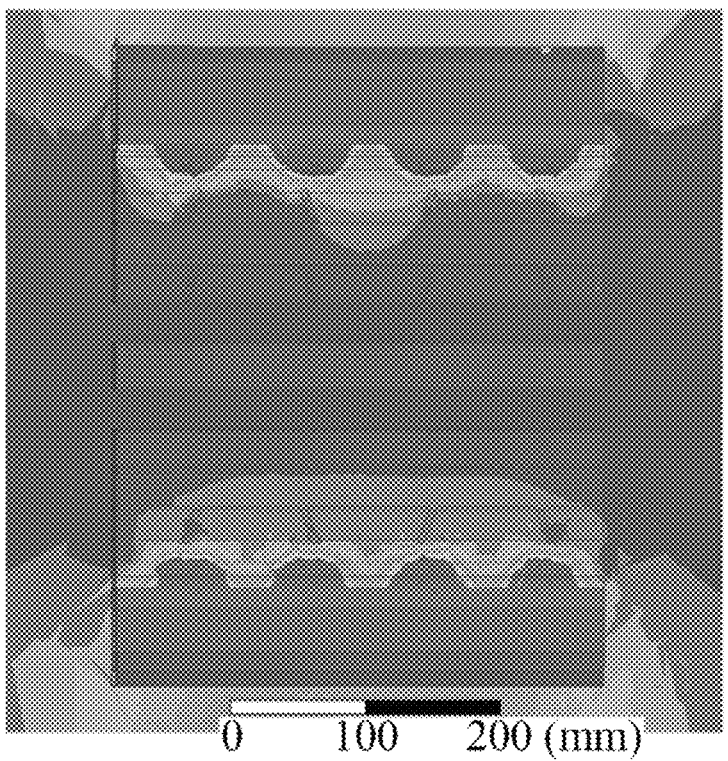
Figure 16F:
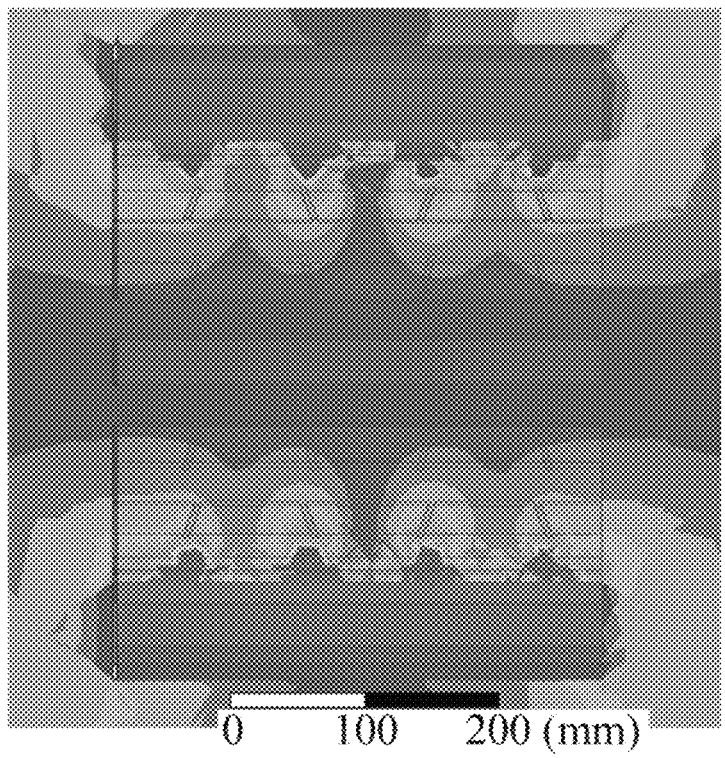

FIGS. 16D-16F show the complex magnitudes the magnetic field components (in T) generated of FIGS. 16A-16C in the sagittal cross section. The $B_1^+$ field component can be observed in FIGS. 16A and 16D; the $B_1^-$ field component can be observed in FIGS. 16B and 16E; and the $B_z$ field component can be observed in FIGS. 16C and 16F.

Figure 17A:
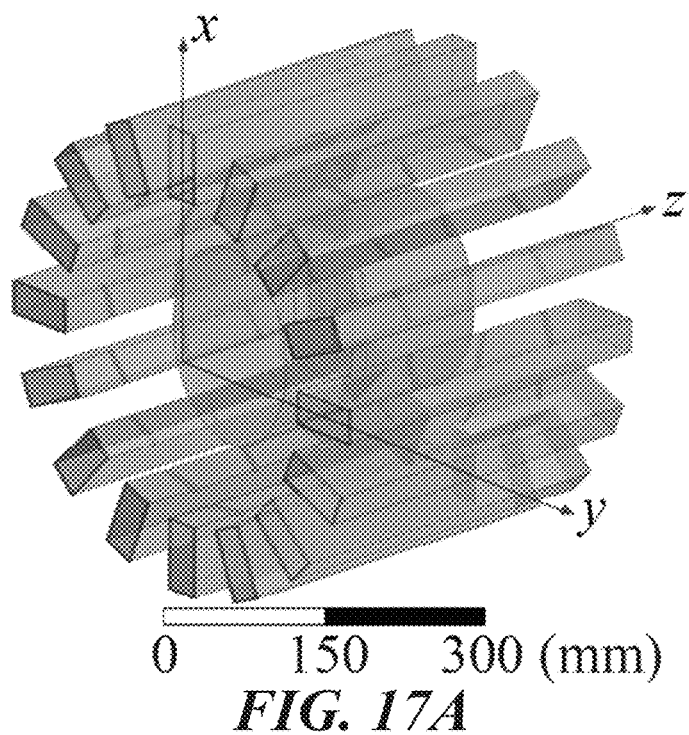
FIG. 17A shows simulation results for a phantom-loaded SWGA RF coil in a 7 T bore with "standard" excitation, in accordance with an illustrative embodiment.

FIG. 17A shows simulation results for a phantom-loaded SWGA RF coil in a 7 T bore with "standard" excitation. The figure shows 16 slotted waveguides around an elliptic-cylinder phantom (metallic bore is not shown).

The study considered a homogeneous dielectric ($\varepsilon_r$=43.776, $\sigma$=0.41335 S/m) elliptic cylinder, acting as a simple phantom (resembling a human head). The long and short radii of the ellipse are 10 cm and 8 cm, respectively, the cylinder is 24 cm long, and it is centered at the center of the array, as shown in FIG. 17A. The SWGA coil and metallic (MRI) bore dimensions are as described in relation to FIG. 15.

Figure 17B:
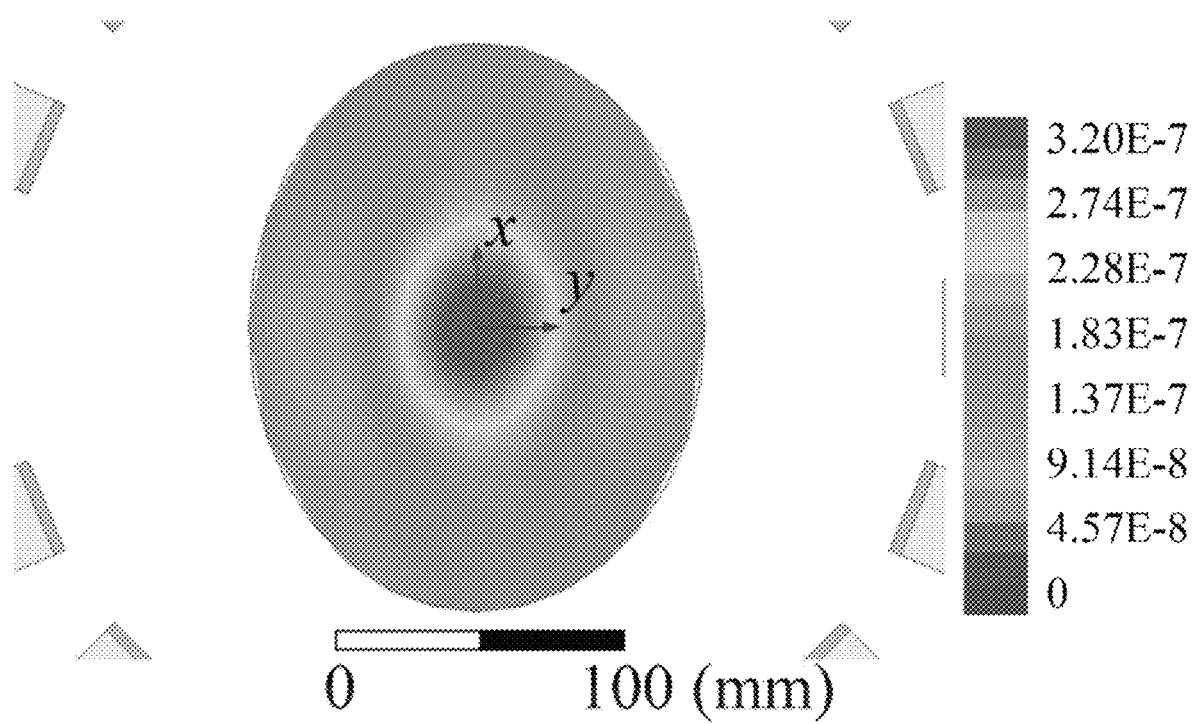
FIGS. 17B and 17C show the simulation results for the transmit efficiency evaluated as $|B_1^+|/\sqrt{P_a}$ $[T/\sqrt{W}]$ and the $|B_1^-|/\sqrt{P_a}$ $[T/\sqrt{W}]$, respectively, of the phantom-loaded SWGA RF coil of FIG. 17A, in accordance with an illustrative embodiment.
Figure 17C:
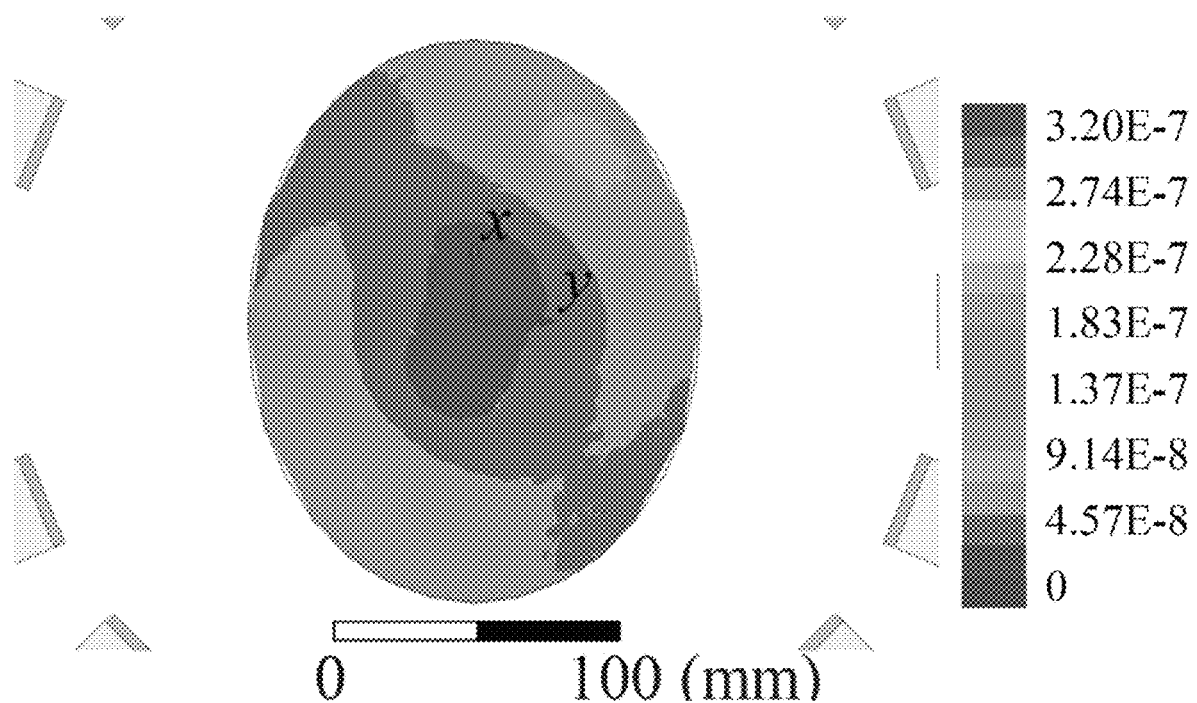

FIGS. 17B and 17C show the simulation results for the transmit efficiency evaluated as $|B_1^+|/\sqrt{P_a}$ $[T/\sqrt{W}]$ (where $P_a$ is the total accepted power for the coil) and $|B_1^-|$ field component, respectively, in the central (at the middle of the phantom) axial cross section of the phantom. It can be seen from the figure that the efficiency peeks at the middle of the cross section at 0.32 $\mu T/\sqrt{W}$, as well as that very low $|B_1^-|$ is maintained in the whole cross section.

With all ports matched to ensure the voltage standing ratio VSWR≤1.3, the computed isolation between the first element and the remaining elements of the array is given in Table 2, noting that similar relations exist for the remaining ports and their mutual isolations. The study concluded from Table 2 that isolation between the elements of the array is between 27 dB and 42 dB, which is excellent and provides a strong basis for both parallel imaging and effective RF shimming.

TABLE 2

| $(-20 \log_{10}|S_{ij}|)$ | | | | | | | |
|---|---|---|---|---|---|---|---|
| 1-2 | 1-3 | 1-4 | 1-5 | 1-6 | 1-7 | 1-8 | 1-9 |
| 29.6 | 38.6 | 31.9 | 28.8 | 29.3 | 40.2 | 31.3 | 28.4 |
| 1-10 | 1-11 | 1-12 | 1-13 | 1-14 | 1-15 | 1-16 | |
| 30.4 | 42.0 | 28.6 | 27.1 | 31.7 | 39.6 | 28.2 | |

Figure 18A:
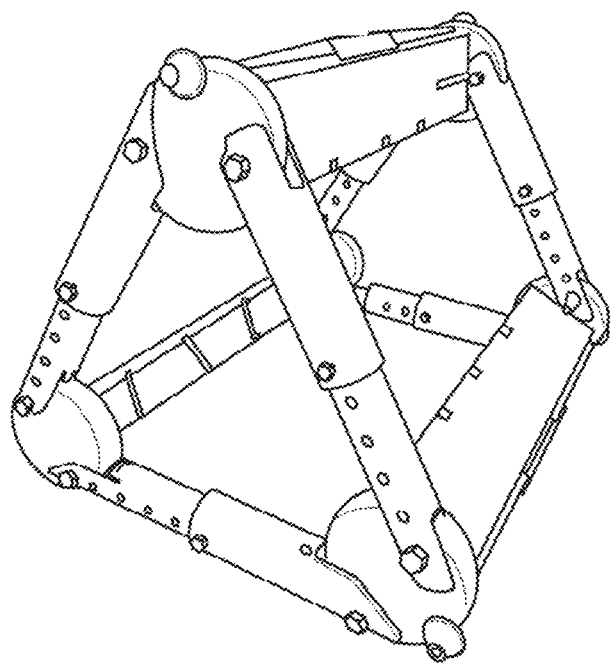
FIG. 18A shows a 3-element SWGA prototype, in accordance with an illustrative embodiment.
Figure 18B:
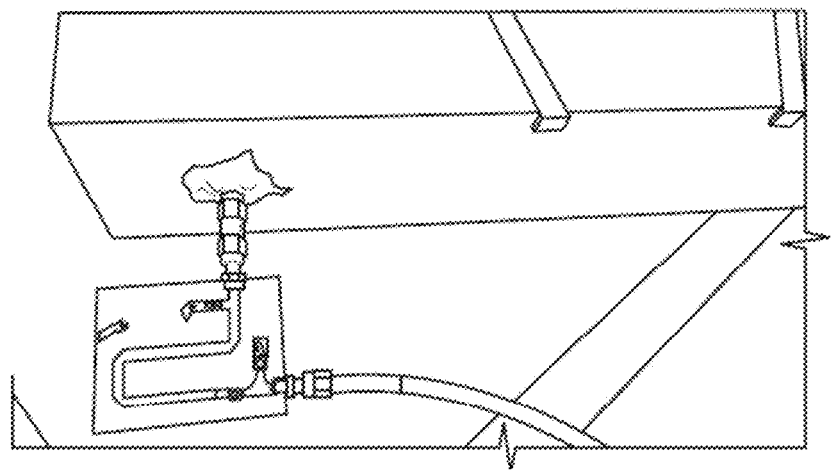
FIG. 18B shows a matching network implemented in the SWGA prototype of FIG. 18A, in accordance with an illustrative embodiment.

FIG. 18A shows a 3-element SWGA prototype. Impedance matching of the slotted waveguides to the nominal impedance of 50Ω was conducted. FIG. 18B shows a matching network implemented in the SWGA prototype of FIG. 18A, in accordance with an illustrative embodiment. As shown in FIG. 18B, a matching network comprises three variable trimmer capacitors with capacitances ranging from 8 pF to 40 pF. Utilizing the designed network, the impedance matching can be practically perfectly tuned. Measured $|S_{11}|$, in free space, was lower than −36 dB. Two waveguides have also been placed next to each other, in open space, to simulate close proximity as if they were arranged in a 16-element array, in FIG. 15, and the measured transmission $|S_{21}|$ between them (coupling) was lower than −33 dB. The measured isolation is even higher between elements in the prototype in FIG. 18A. As shown in FIGS. 18A and 18B, the prototype waveguides are filled with a dielectric (i.e., water) and sealed (e.g., with 3D printed corks that are glued via epoxy at the slots).

Figure 18C:
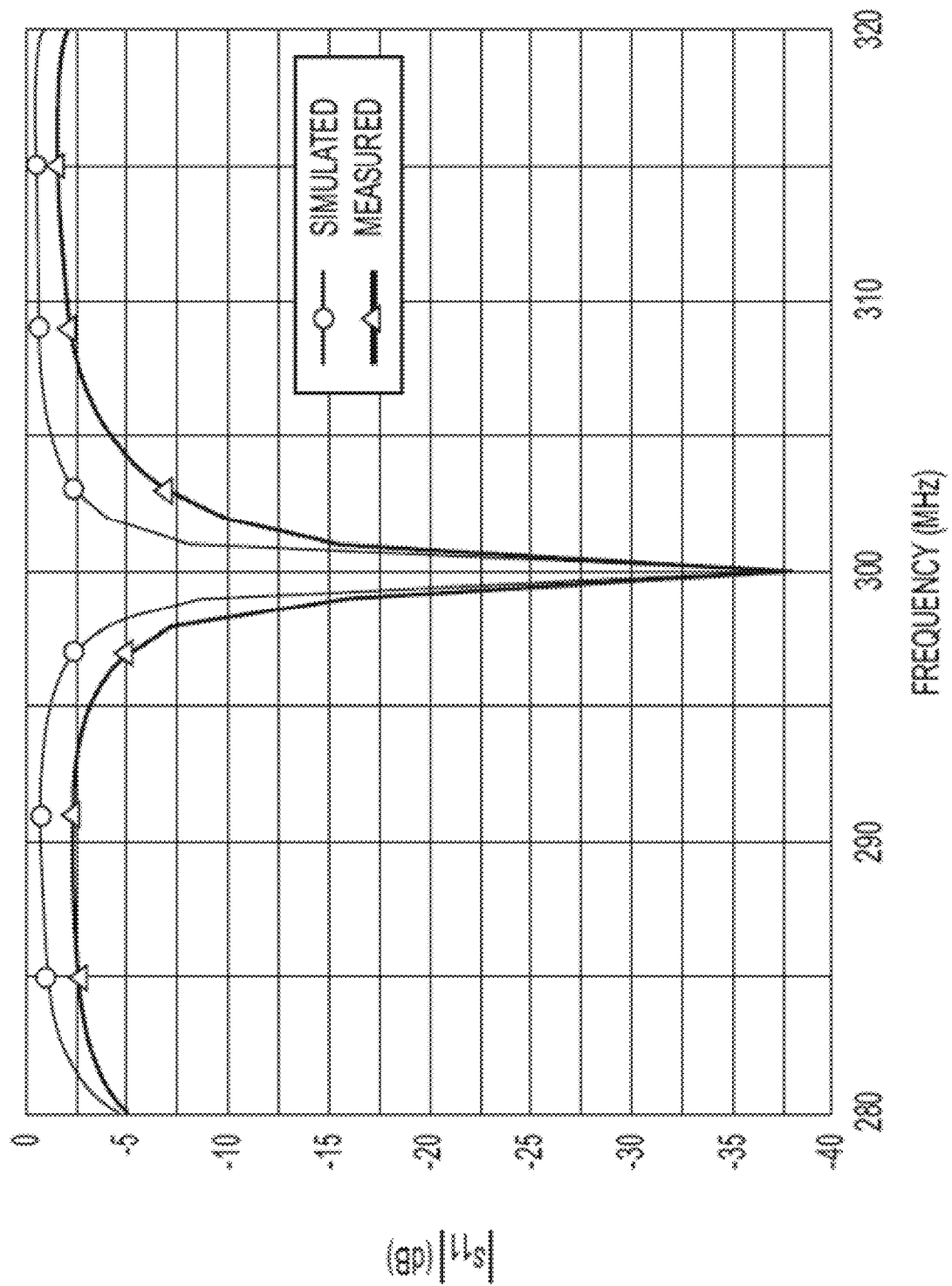
FIG. 18C shows simulated and measured reflection coefficient of a single matched slotted-waveguide element, in accordance with an illustrative embodiment.

FIG. 18C shows simulated and measured reflection coefficient of a single matched slotted-waveguide element, in accordance with an illustrative embodiment. The figure shows both simulated (in a bore) results and the worst case (of the 3 built prototypes) bench-measured results (in free space). Simulated and measured Q-factors are about 120 and at least 50, respectively.

As can be seen from FIG. 18C, the 2 sets of reflection coefficient results, via simulations and bench measurements, are in a very good agreement. Lower measured Q-factor is primarily attributed to the fact that water in waveguides causes corrosion of the waveguide walls and aluminum particles dissolved in water introduce additional loss. It is also noticed that the lowering of the measured Q-factor over time. Both problems can be solved in the future by coating the waveguide walls or using different low-loss dielectric (with similar dielectric constant, e.g., based on titanium-oxide powers) inside the waveguide.

Array of $N_a$ independently driven antennas enables efficient RF shimming by means of adjusting the magnitudes and phases of excitations, i.e., by adjusting $2N_a$ independent variables. The system can adjust excitations using various criteria for optimization of the field distribution. Some typical optimization goals include maximization of (i) $B_1^+$ field strength or (ii) its uniformity, which, in turn, can be optimized (maximized) in (iii) a local domain, (iv) globally, or (v) in certain cross sections. The system can perform the optimization using various methods including those described in W. Mao, M. B. Smith, and C. M. Collins, "Exploring the limits of RF shimming for high-field MRI of the human head," Magnetic Resonance in Medicine, vol. 56, pp. 9 18-922, 2006, or the least-square techniques described in H. P. Hetherington, N. I. Avdievich, A. M. Kuznetsov, and J. W. Pan, 'RF shimming for spectroscopic localization in the human brain at 7 T," Magnetic Resonance in Medicine, vol. 63, pp. 9-19, 2010; or the gradient and genetic algorithms described in T. S. Ibrahim and L. Tang, "Insight into RF power requirements and $B_1$ field homogeneity for human MRI via rigorous FDTD approach," Journal of Magnetic Resonance Imaging, vol. 25, pp. 1235-1247, 2007, each of which is incorporated by reference herein in its entirety.

Figure 19A:
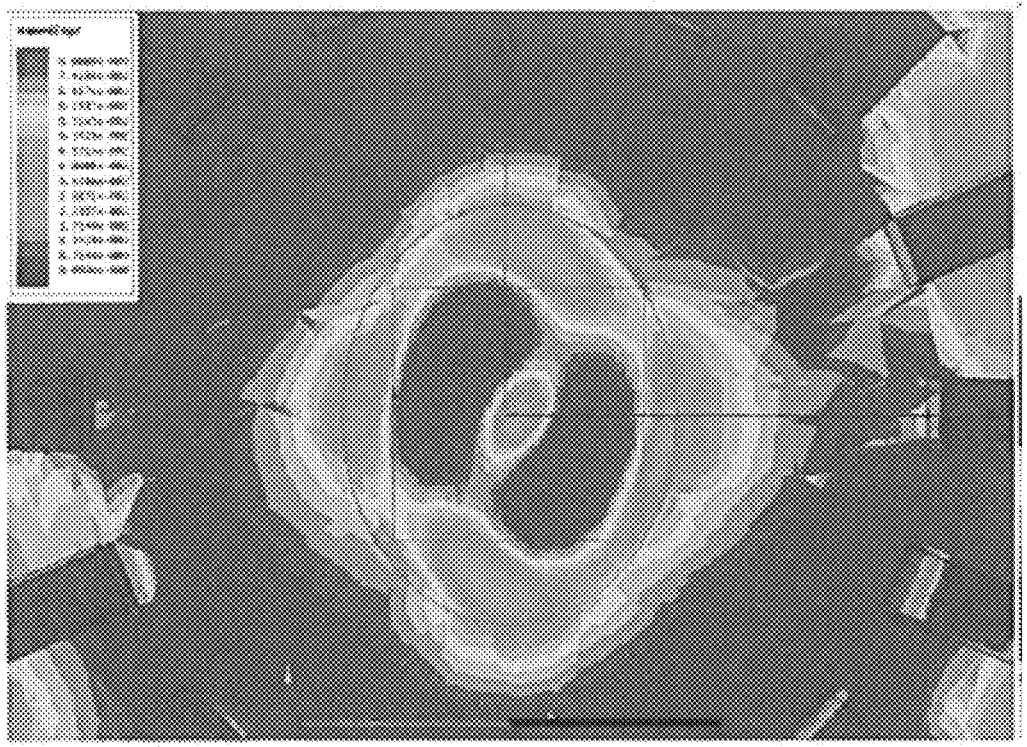
FIGS. 19A and 19B show simulation results of $|B_1^+|$ field and $|B_1^-|$ field, respectively, for the phantom-loaded SWGA RF coil of FIG. 17A.
Figure 19B:
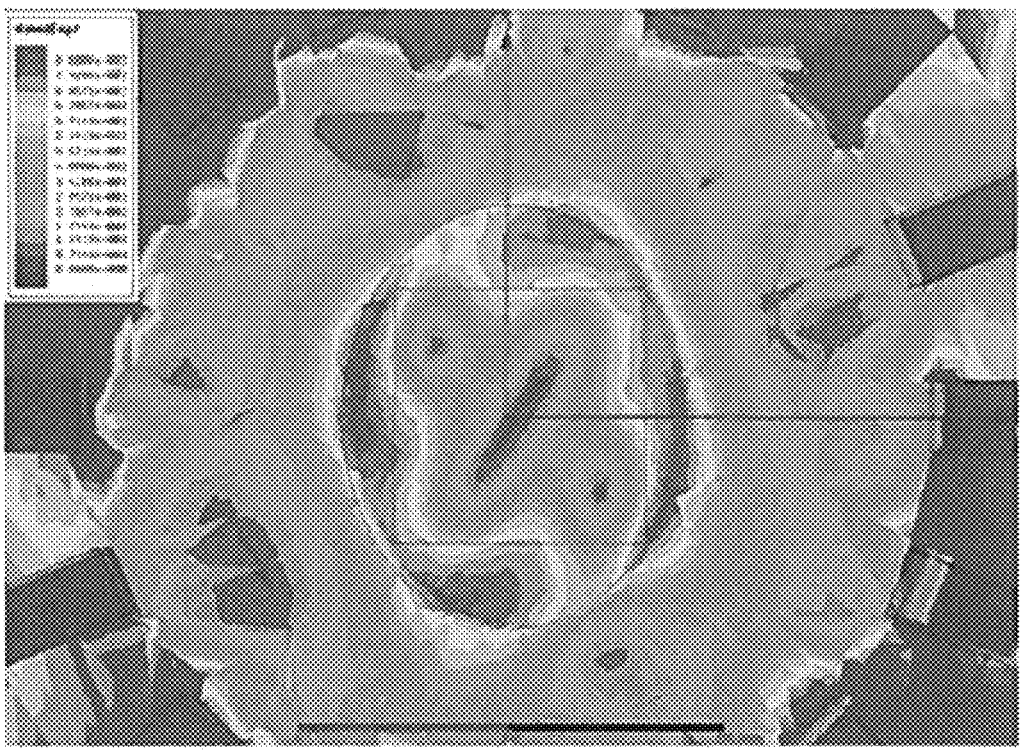

FIGS. 19A and 19B show simulation results of $|B_1^+|$ and $|B_1^-|$ field, respectively, for a phantom-loaded SWGA RF coil at 7 T after shimming. The results are of an optimization of the structure from FIG. 17A, obtained by applying the Nelder-Mead algorithm with a goal to improve the uniformity of $B_1^+$ field, while maintaining very low $|B_1^-|$. The fields are in au., normalized to respective maxima. The optimization region is a square in the middle of the phantom, located in the considered axial cross-section and shown in FIGS. 19A and 19B. It can be seen from the figure that much more uniform $B_1^+$ can be easily obtained by shimming, while keeping $|B_1^-|$ significantly low. This optimization lasted less than 2 min on a very modest Core i5-based PC.

To provide more robust optimizations, the study also evaluated utilization of genetic algorithms, because a very large optimization space arises in presented applications.

To further improve the efficiency of the exciter, the study employ use of a low-loss high-permittivity dielectric on each of the slotted waveguides, in front and surrounding the slotted waveguide side, as shown in FIG. 12. The role of the dielectric is to provide a sort of smoother impedance transition from slots into free space and reduce the backward radiation. In a sense, the dielectric performs as a basic lens, facilitating focusing of the radiation in the desired direction. Alternatively, a lens of optimized shape and dielectric profile, or array of lenses, can be utilized as well.

Figure 20A:
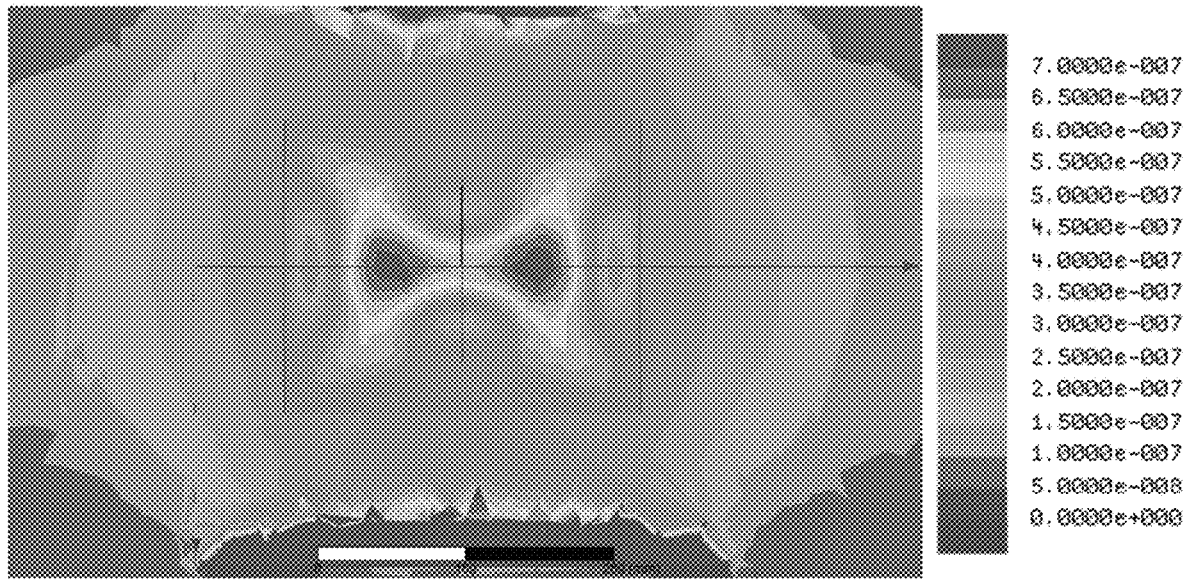
FIGS. 20A and 20B show comparison of efficiencies obtained by a baseline 16-element "stripline" TEM coil and by the 16-element SWGA coil with dielectric lenses in imaging of the saline, in accordance with an illustrative embodiment.
Figure 20B:
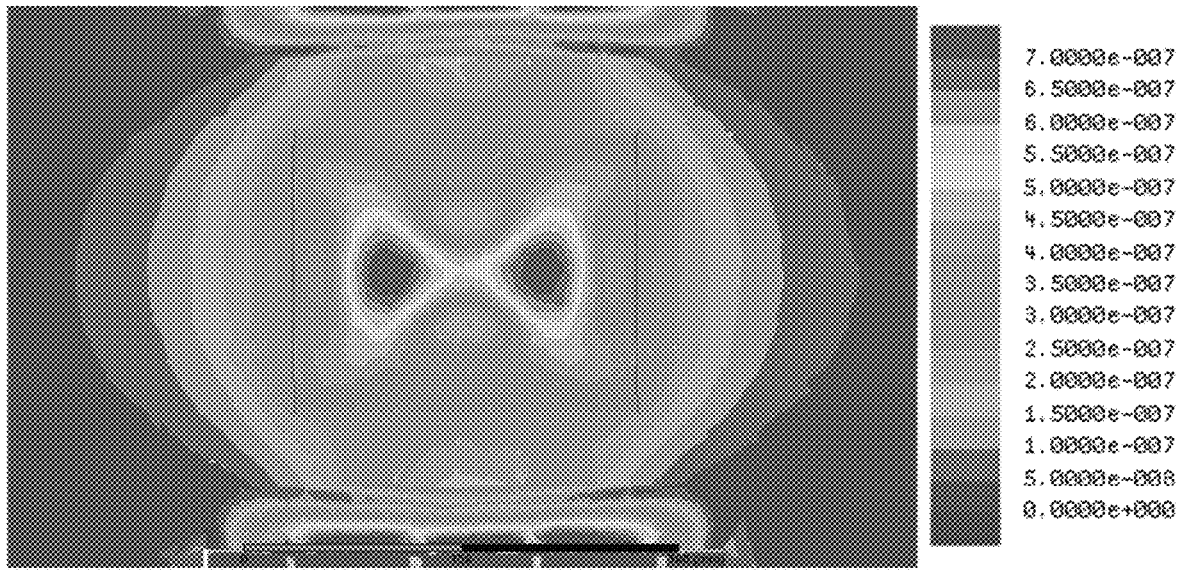

FIGS. 20A and 20B show comparison of efficiencies obtained by a baseline 16-element "stripline" TEM coil (FIG. 20A) and by the 16-element SWGA coil (FIG. 20B) with dielectric lenses in imaging of the saline ($\varepsilon_r$=82, σ=0.6 S/m) phantom having the same dimensions as described in relation to FIG. 15. The color code in FIGS. 20A and 20B is adjusted to show the full span of obtained efficiencies in both cases. The "stripline" coil is described in detail in G. Adriany, P.-F. Van de Moortele, F. Wiesinger, S. Moeller, J. P. Strupp, P. Andersen. et al., "Transmit and receive transmission line arrays for 7 Tesla parallel imaging," Magnetic Resonance in Medicine, vol. 53, pp. 434-445, 2005.

It can be seen from the figures that both arrays produce similar field distribution. However, the SWGA array produces maximum efficiency of about 1.1 µT/√W, whereas it is about 0.7 µT/√W for the TEM array, yielding approximately 57% improvement obtained by the exemplary exciter array. This efficiency performance of the exemplary exciter array is greater than all of those have been reported in state-of-the-art systems.

Figure 21A:
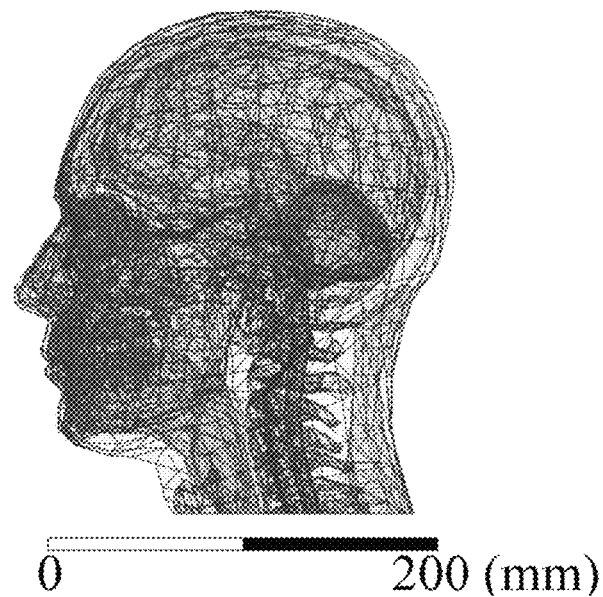
FIG. 21A shows a human head phantom model used in an analysis of a SWGA coil of FIG. 15 used in an MRI bore at 7 T, in accordance with an illustrative embodiment.
Figure 21B:
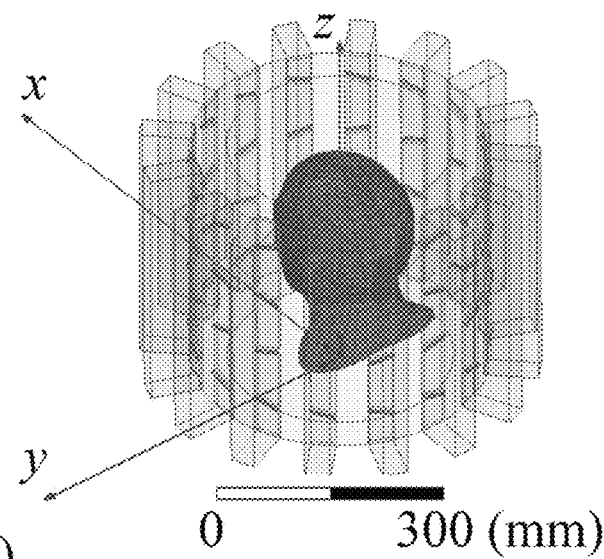
FIGS. 21B, 21C, and 21D each shows different views (perspective, front, and side views) of the head model inside the SWGA coil of FIG. 21A, in accordance with an illustrative embodiment.
Figure 21C:
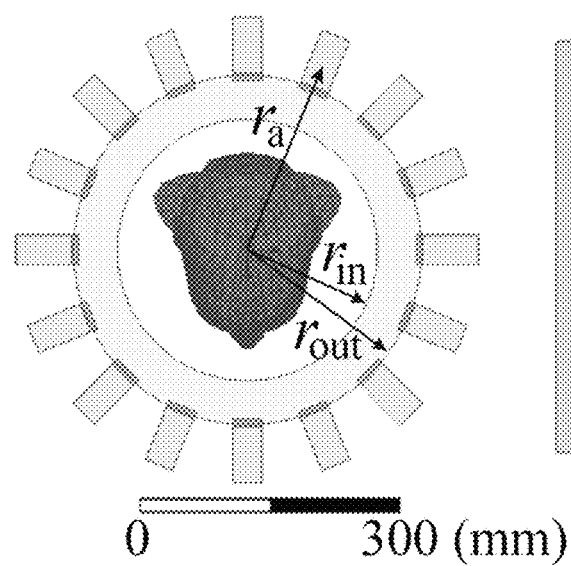
Figure 21D:
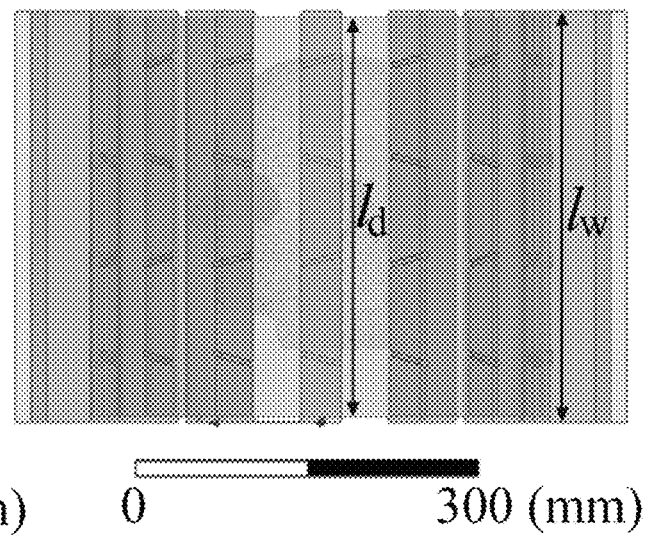

FIG. 21A shows a human head phantom model used in an analysis of a SWGA coil of FIG. 12 used in an MRI bore at 7 T. FIGS. 21B, 21C, and 21D each shows different view of the head model inside the SWGA coil of FIG. 21A.

The study also considered a 12-tissue human head model 220 mm long from the tip of the nose to the back of the scull, as shown in FIG. 21A. The head is positioned inside the SWGA as depicted in FIG. 21B. The array also comprises a hollow dielectric ($\varepsilon_r$=30) cylinder (a lens) whose outer cylindrical surface covers the waveguide slots, as shown in FIGS. 21B and 21C, with the same purpose as the lens in FIG. 12. The bore, waveguides comprising the array, and their position in the bore are the same as described in relation to FIGS. 15 and 21A-21D, with the exception of the array radius, which is set to $r_a$=230 mm. The inner and outer radii of the dielectric lens are $r_{in}$=150 mm and $r_{out}$=200 mm, respectively. The height of the lens is $l_d$=350 mm and it is placed symmetrically with respect to the array, as shown in FIG. 21D.

Figure 22A:
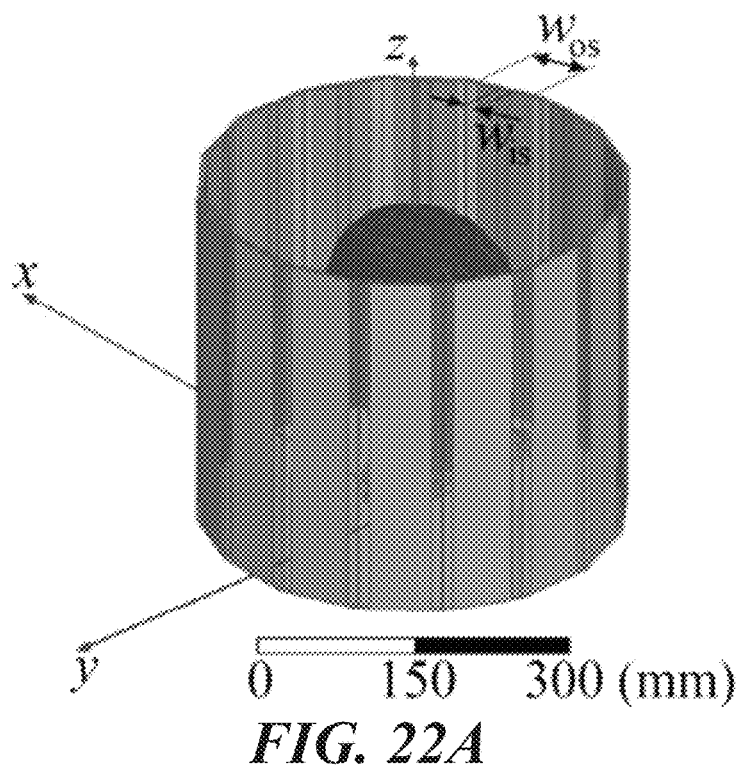
FIG. 22A shows a human head phantom model used in an analysis of a stripline array used in comparison to the analysis of a SWGA coil of FIGS. 21A-21D.
Figure 22B:
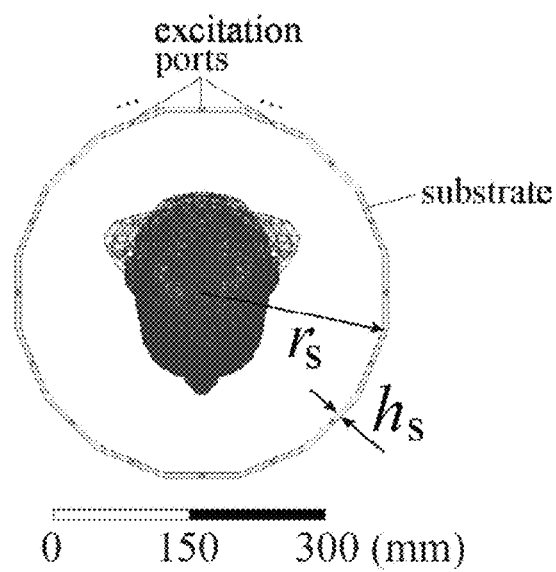
FIGS. 22B and 22C each shows different views (front and side views) of the head model inside the SWGA coil of FIG. 22A.
Figure 22C:
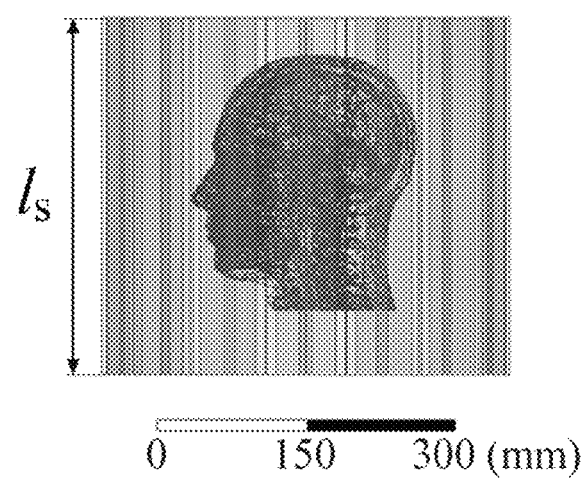

To facilitate correct and as fair as possible comparison with one of the alternative highly efficient RF array coils, the study construct a model of a 16-element "stripline" TEM circular array closely resembling the array utilized in Adriany et al., "Transmit and receive transmission line arrays for 7 Tesla parallel imaging". The array with the head model is shown in FIG. 22A and it is also positioned at the center of the metallic bore. FIG. 22A shows a human head phantom model used in an analysis of a stripline array used in comparison to the analysis of a SWGA coil of FIGS. 21A-21D. FIGS. 22B and 22C each shows different view of the head model inside the SWGA coil of FIG. 22A.

As shown in FIGS. 22A-22C, the height of the "stripline" array is $l_s=l_w=360$ mm, the radius (from the center of the array to the middle of the dielectric substrate) is $r_s=200$ mm, and the widths of the outer and inner copper strips are $w_{os}=60$ mm and $w_{is}=12$ mm, respectively. The strips are considered to be infinitely thin. Feeding of the strips is with the same phase shifts as applied to SWGA coil (e.g., $-2\pi/16$ between the excitations of adjacent elements in the clockwise direction). Dielectric substrate carrying the strips is $h_s=5$ mm thick Teflon (dielectric constant and loss tangent are $\varepsilon_r=2.1$ and $\tan \delta=0.001$, respectively).

Figure 23A:
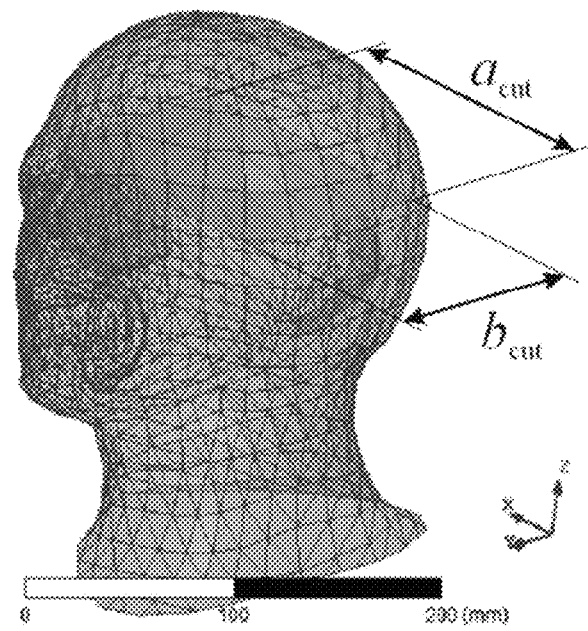
FIGS. 23A-23C show sagittal cross-section of the cranium used in an investigation of efficiency of the SWGA exciter with a human head.
Figure 23B:
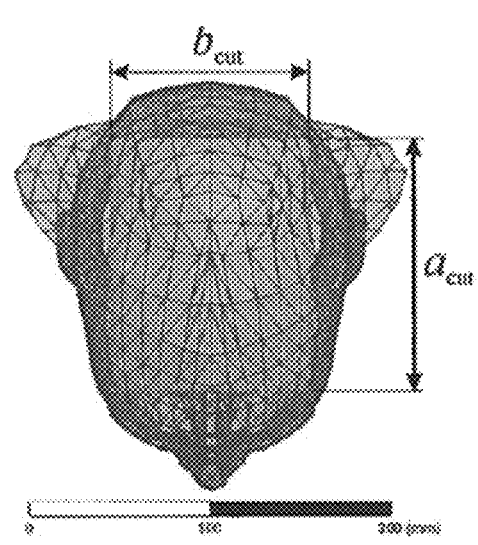
Figure 23C:
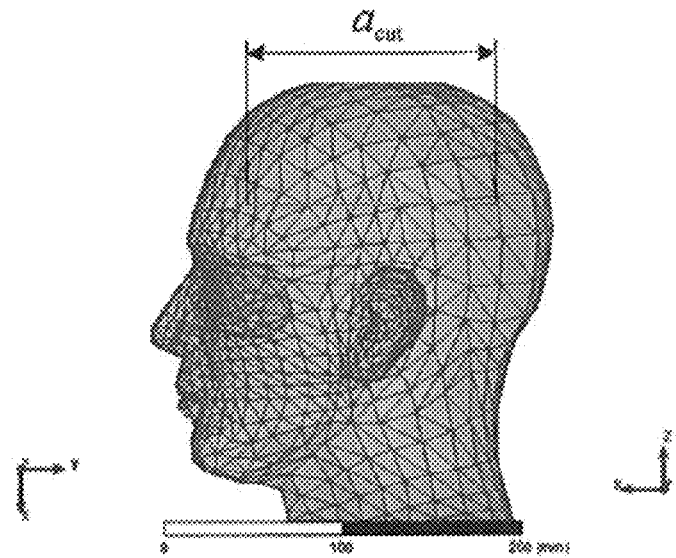

The study also investigated the efficiency of the SWGA exciter with a human head model. To simplify the investigation, the study focused on the axial cross section of the cranium, depicted in FIGS. 23A-23C, and on the sagittal cross section of the head. FIGS. 23A-23C show sagittal cross-section of cranium used in an investigation of efficiency of the SWGA exciter with a human head. A symmetrically placed rectangular cut in the same axial cross section, depicted in FIGS. 23A-23C, is later used for optimization of the field uniformity by RF shimming. The sides of the rectangular cut are $a_{cut}=110$ mm and $b_{cut}=140$ mm.

Figure 24A:
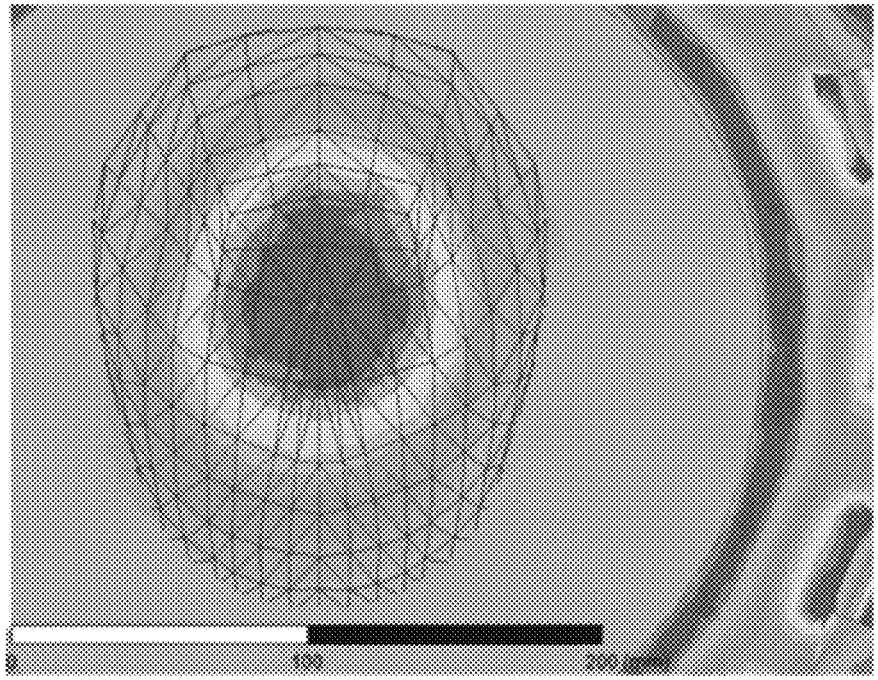
FIGS. 24A and 24B each presents simulated efficiency $|B_1^+|/\sqrt{P_a}$ [T/√W] of the SWGA exciter from FIGS. 21A-21D along the sagittal cross-section shown in FIGS. 23A-23C, in accordance with an illustrative embodiment.
Figure 24B:
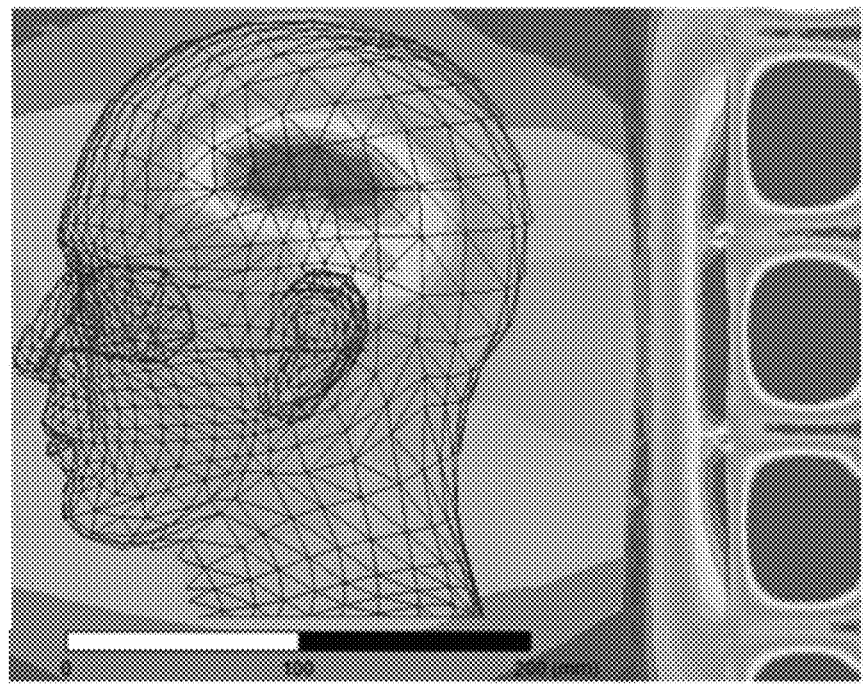
Figure 24C:
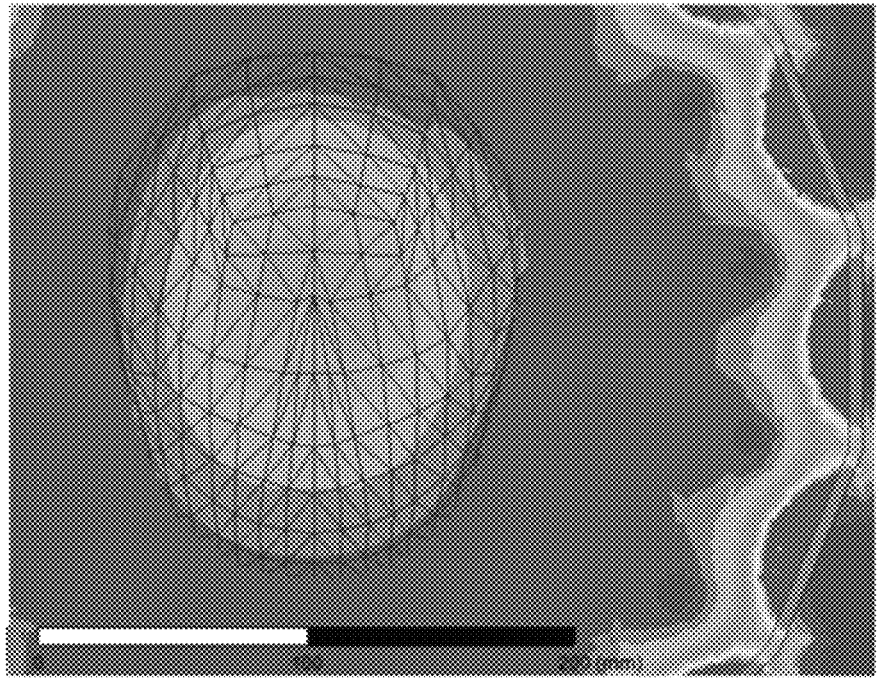
FIGS. 24C and 24D each presents simulated efficiency $|B_1^+|/\sqrt{P_a}$ [T/√W] of the microstrip coil of FIGS. 22A-22C along the sagittal cross-section shown in FIGS. 23A-23C, in accordance with an illustrative embodiment.
Figure 24D:
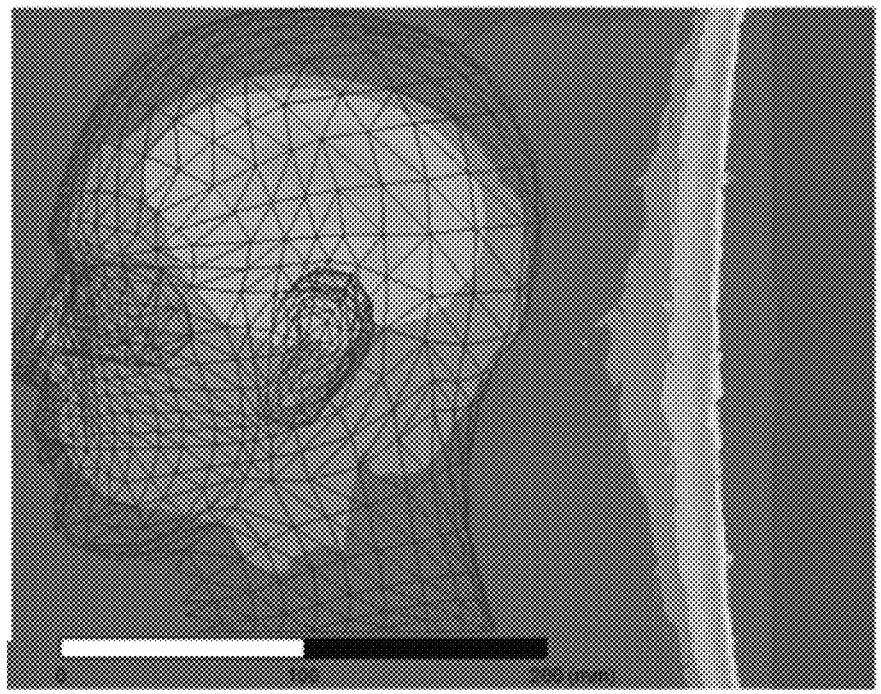

FIGS. 24A and 24B each presents simulated efficiency $|B_1^+|/\sqrt{P_a}$ [T/√W] of the SWGA exciter from FIG. 21B. For comparison, FIGS. 24C and 24D show the simulated efficiency of the "stripline" TEM array from FIG. 22A. The study concluded per the results in FIGS. 24A-24D that the overall field distributions in both axial and sagittal cross sections are practically the same for both arrays. However, the efficiency of the SWGA exciter (FIGS. 24A and 24B) is much higher than that of the "stripline" array (FIGS. 24C and 24D). Specifically, the peak efficiency obtained by the SWGA coil is 2.39 µT/√W, whereas for the TEM coil it is about 1.0 µT/√W. Indeed, in this comparison, the SWGA coil provides 130% improvement in the (computed) efficiency over the TEM coil, while providing practically the same field distribution in the head model phantom.

Comparison of the transmit efficiencies with several results found in the literature is given in Table 3, including those from A. Andreychenko, et al., "Improved steering of the RF field of traveling wave MR with a multimode, coaxial waveguide," Magnetic Resonance in Medicine, vol. 71, pp. 1641-1649, 2013; A. Andreychenko, et al., "Coaxial waveguide for travelling wave MRI at ultrahigh fields," Magnetic Resonance in Medicine, vol. 70, pp. 875-884, 2012; D. O. Brunner et al., "Traveling-wave RF shimming and parallel MRI," Magnetic Resonance in Medicine, vol. 66, pp. 290-300, 2011; B. Zhang et al. "Whole body traveling wave magnetic resonance imaging at high field strength: Homogeneity, efficiency, and energy deposition as compared with traditional excitation mechanisms," Magnetic Resonance in Medicine, vol. 67, pp. 1183-1193, 2012; and C. J. Snyder et al., "Comparison between eight- and sixteen-channel TEM transceiver arrays for body imaging at 7 T," Magnetic Resonance in Medicine, vol. 67, pp. 954-964, 2012.

TABLE 3

| Coil Type | Reported transmit efficiency [µT/√W] | Type | Reported transmit efficiency [µT/√W] | Type |
|---|---|---|---|---|
| Slotted waveguide array | 2.39 | Peak quadrature | 1.74 | Peak Shimmed |
| Coaxial Waveguide | 0.44 | Head quadrature | 0.07 | Head Shimmed |
| Coaxial Waveguide | 0.30 | Cylindrical quadrature | 0.12 | Head |
| Traveling wave array with rods | 0.158 | Peak | | |
| TEM resonator | 0.16 | Peak | | |
| Transmission line array | 0.27 | | | |

The study concluded that the exemplary SWGA exciter yields higher efficiencies than all those reported in the literature.

To demonstrate the use for RF shimming of the SWGA coil with the exemplary SWGA exciter, the study used a rectangular cut in the axial cross section, shown in FIGS. 23A-23C, in which a coarse uniform grid of 21×21 points was considered for explicit evaluation of the field. The study first evaluates the efficiency for the "standard" (nominal) excitation and then optimize the excitations to minimize deviation of the efficiency in the established grid by running a genetic algorithm. The 31-dimensional optimization space comprises 16 excitation magnitudes (i.e., incident powers) and 15 phases (arguments of the complex excitations). The phase of one (e.g., the first) excitation was fixed to reduce the optimization space and prevent periodic solutions. Descriptive statistics of the computed efficiencies is shown in Table 4.

TABLE 4

| Excitation | Mean [µT/√W] | Std. Dev. (SD) [µT/√W] | Minimum [µT/√W] | Maximum [µT/√W] |
|---|---|---|---|---|
| Standard | 1.51 | 0.48 | 0.56 | 2.39 |
| Optimized | 1.10 | 0.31 | 0.50 | 1.74 |

It can be seen from Table 4 that the optimization yielded an improvement of 35.4%, while providing an optimized field uniformity results that did not reduce overall efficiency.

Figure 25A:
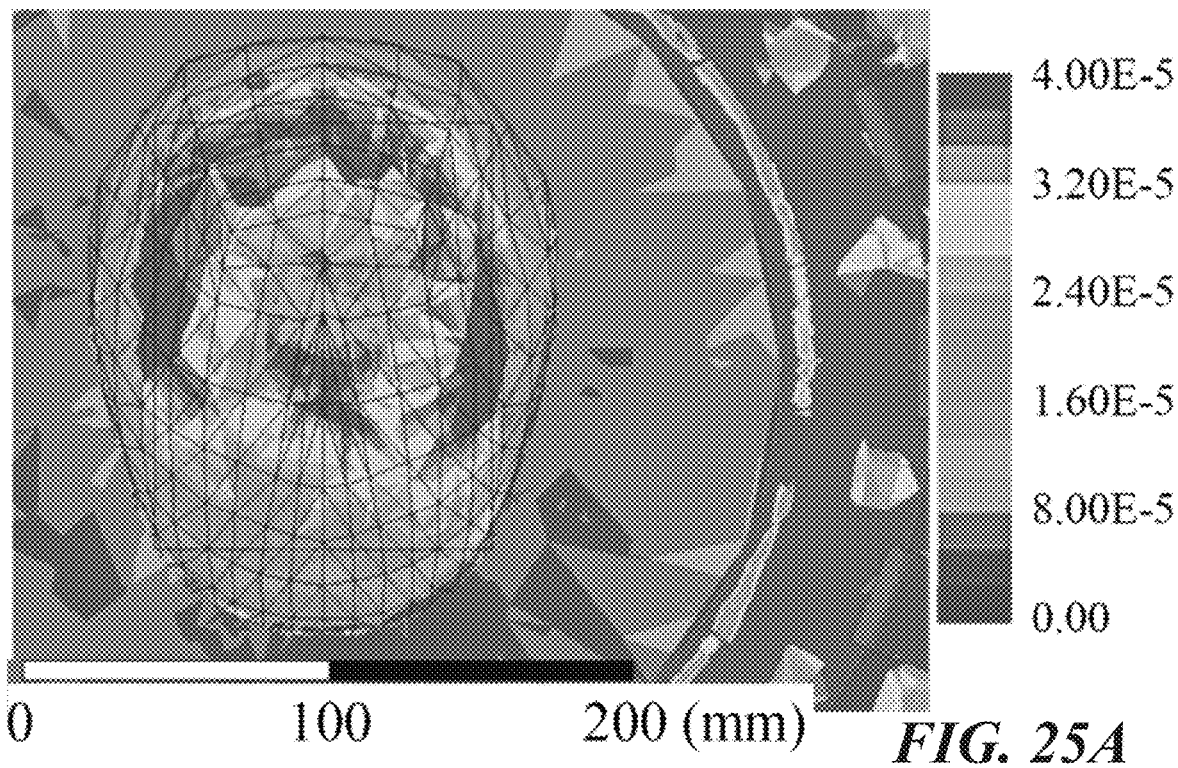
FIGS. 25A and 25B show magnitude of efficiency gradient $|\nabla|B_1^+||/\sqrt{W}$ obtained by the exemplary SWGA RF coil using a standard excitation (FIG. 25A) and an optimized excitation (FIG. 25B) with a head model described in relation to FIGS. 21A-21D, in accordance with an illustrative embodiment.
Figure 25B:
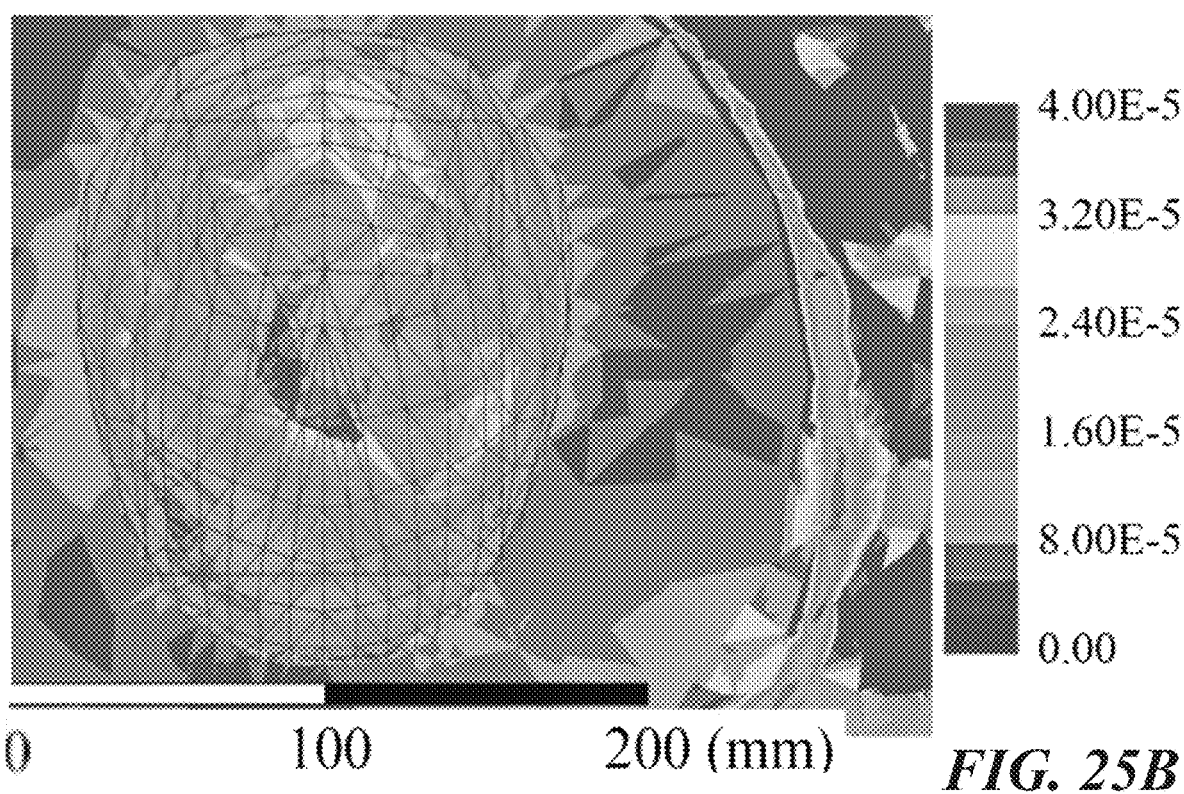

FIGS. 25A and 25B show magnitude of efficiency gradient $|\nabla|B_1^+||/\sqrt{W}$ obtained by the exemplary SWGA RF coil using a standard excitation (FIG. 25A) and an optimized excitation (FIG. 25B) with a head model described in relation to FIGS. 21A-21D.

As a graphical representation of the RF shimming effect, FIGS. 25A and 25B are presented with the magnitude of the efficiency gradient before and after optimization. It can be seen from FIGS. 25A and 25B that RF shimming of the SWGA coil can indeed significantly improve the field uniformity in the imaged subject.

Indeed, a preliminary numerical study of applicability of slotted waveguide arrays as RF exciters for ultra-high field MRI shows that the exemplary arrays can efficiently generate circularly polarized magnetic fields, highly desirable for good quality imaging. The observed efficiency of the array in the human head experiment was over 2 µT/√W whereas it was lower than 0.5 µT/√W in all results reported in the literature. Configuration of the slots from FIGS. 2 and 12 can be optimized for the certain environment to yield maximum radiation efficiency without influencing the purity of polarization. In particular, distances $l_i$, $i=1, \ldots, N_s$, and the slot angle $\theta$ can be varied to achieve the required radiation properties and impedance matching. In addition, if detuning of the antennas is required, it can be done using PIN diodes. Indeed, the waveguides can be made shorter or longer, incorporating fewer or more slots, depending on the desired FOV.

As noted above, exemplary slotted-waveguide RF coil can provide RF magnetic field $B_1^+$ with high field-uniformity, high efficiency, excellent circular polarization, negligible axial z-component, arbitrary large field of view, and exceptional possibilities for field-optimizations via RF shimming.

Indeed, it is generally desired in the design of RF coils that the coil provides good circular polarization, RCP, along the axis of the bore and the phantom (z-axis) for the transverse components (normal to the axis of the bore and to field $B_0$) of the magnetic field $B_1$, that is, $B_1^+$, quantified as a low (close to unity) value of the axial ratio, AR, defined as the ratio of the major and minor axes of the polarization ellipse of the transverse $B_1$ field (AR 1). For a purely (ideally) circularly polarized field, AR=1 (or 0 dB), and AR close to unity in MRI applications indicates a very predominant RCP component of the transverse $B_1$, $B_1^+$, over the left-hand CP (LCP) component, $B_1^-$, and hence a high value of the ratio $B_1^+/B_1^-$.

Further, it is generally desired that the design provides as much circularly polarized (RCP) transverse $B_1$ field and as low (close to 1) AR and as high ratio $B_1^+/B_1^-$ as possible elsewhere in the phantom (or subject that is imaged). Circularly polarized $B_1$ field, with AR=1 and equal powers in the two transverse components (x and y components), is desirable. The more circularly polarized $B_1$ field the higher the resulting SNR. A linearly polarized (LP) field would require too much RF deposition to get the same SNR as compared to a modest power with a CP $B_1$ field. Hence, LP B1 fields are undesirable.

It is also generally desired that the design provides high spatial uniformity of the transverse $B_1^+$ field along the z-axis. It is also generally desired that the design provides good efficiency, characterized by $|B_1^+|/\sqrt{P_a}$ where $P_a$ is the total accepted RF power. It is also generally desired that the design provides low (ideally 0) axial $B_1$ field (z-component of $B_1$). It is also generally desired that the design provides as uniform as possible RCP transverse field, $B_1^+$, elsewhere in the phantom (subject). Transverse $B_1^+$ field uniformity is directly related to the resulting MRI image quality. The polarizing static field $B_0$ can be shimmed to very high uniformity using shim coils ($B_0$ shimming is done automatically during system initialization prior to imaging), so that any image nonuniformity is due to the transverse B1 field nonuniformity. It is also generally desired that the design allows for multichannel excitation with highly decoupled channels to facilitate parallel imaging and RF shimming by different feeding patterns to achieve optimal $B_1^+$ field distribution within the imaging subjects. In the exemplary slotted-waveguide RF coil, excitations are decoupled because the waveguides can be decoupled. The excitation sequence can be tailored to ensure proper (right-handed or left-handed) circularly polarized RF magnetic field in the desired region. Typically, in an empty bore, the array of N waveguides can be excited with identical incident powers, successively phase-shifted by $-2*\pi/N$ to produce a uniform circularly, polarized, transverse (to z) RF magnetic field along the array axis (z-axis) and in its vicinity.

It is also generally desired that the design allows for easy detuning (e.g., for receiving by external probes). It is also generally desired that the design provides strong coupling of the field/wave with the phantom (subject) and strong field penetration in the entire phantom. It is also generally desired that the design provides local SAR at every point in the body (phantom), found as $\sigma(r)|E(r)|^2/\rho(r)$, with $\sigma$ standing for the conductivity and $\rho$ for the mass density of the tissue, as well as averaged total SAR values for individual organs and areas, should be, for the given total input RF power of the system, well below the acceptable and allowable prescribed SAR levels, to prevent any potential health hazards. Note that any component of the $B_1$ field in the z-direction does not impact image quality but will ultimately lead to undesirable increase in RF deposition and SAR (heating) in the imaging volume, so it is desirable to minimize that component as a result.

Discussion

In 3 T clinical MRI scanners, the field $B_1$ is generated by an RF exciter—the so-called RF coil—almost exclusively in the form of a birdcage coil. The birdcage RF coil consists of two circular metallic loops (end rings) in transversal planes connected by an even number of longitudinal (along the bore axis) straight metallic segments (legs), with lumped capacitors placed along the rings between each pair of adjacent legs. The structure is fed via two excitation ports in time-phase quadrature (90° out of phase with respect to one another). The time-harmonic (steady-state sinusoidal) currents at the given Larmor frequency (e.g., 127.8 MHz for a 3-T scanner) flowing along longitudinal legs are sequentially phase-shifted around the transversal rings, with the phase shift between the currents in neighboring legs amounting to 360° divided by the number of legs, to generate an RCP $B_1^+$. While whole-body birdcage coils are mostly used only as RF transmitters with local surface coils as receivers, smaller bird-cage coils (e.g., head and extremity coils), which are closer to the imaged objects/tissues, are often used as both RF transmitters and receivers. The $B_1$ RF field normally used in MRI, including all 3 T clinical MRI scanners, is in near-field mode of operation. The birdcage coil is typically a near-field (quasi-static) RF coil. Several recent attempts to improving homogeneity of whole-body coils in pre-clinical scanners at higher fields ($B_0$>3 T) include various modifications of birdcage: TEM, spiral coils that still operate in near-field regime.

Next-Generation Ultra-High-Field (UHF) MRI Systems. Since its inception, MRI has operated in the long-wavelength (quasi-static) regime where radio-frequency (RF) wavelength is much larger than the imaged sample. With the advent of ultra-high field (UHF) human imagers, however, given the high dielectric constant, $\epsilon r$, of tissues, the excitation wavelength becomes on the order of, or smaller than, the imaged sample, resulting in a fairly complex mix of nearfield and far-field RF behaviors. Namely, at $B_0$=7 T, with typically about 50-55 in biological samples at this Larmor frequency (~300 MHz), the RF wavelength inside tissues is about 14 cm or less. Because of this short wavelength, complex RF phase modulation and interference phenomena, commonly observed at microwave and optical frequencies but traditionally negligible in MR experiments, are readily observed in tissues at UHF. In practice, biological tissues behave like lossy dielectrics, resulting in a complex superposition of multiple propagating mode excitation intermixed with RF penetration attenuation, yielding highly nonuniform excitation magnetic field ($B_1$) distribution, an issue quickly identified as one of the main challenges to develop UHF MRI technology in humans Notable attempts, as reported in literature, to generate a more uniform $B_1^+$ field with a body coil at 7 T with a TEM body coil were not successful. Twisting a birdcage volume coil structure towards a spiral shape has been proposed to distribute RF phase through space; however, this was for head RF excitation and only at 4 T, thus in this instance, RF interactions were still dominated by a near-field or quasi-static regime. At UHF, excitation probes essentially operate as antennas, in place of the traditional quasi-static, near-field RF coils. Whereas most clinical scanners operate at 1.5 T or 3 T, cutting-edge centers in neuroscience and/or MR imaging more and more tend to acquire UHF scanners because higher $B_0$ values yield higher signal-to-noise ratio (SNR), that can be traded for higher spatial resolution, as well as higher parallel imaging performances allowing for higher acquisition acceleration factor. Also, the UHF systems can provide increased sensitivity and functionality of MRI overall.

The main area of engineering research in advancing MRI scanners is in improving RF coils and fields, i.e., in enhancing the generation and control of B1 RF fields inside an MRI bore and a phantom (or a subject under MRI imaging). Examples of RF coils other than birdcage coils, that can be used for ultra-high-field (UHF) MRI, include excitation using loops, dipole antennas, microstrip patch antennas, etc. as antenna probes, as well as various dielectric and other material loadings incorporated into the bore to reduce the cutoff frequencies of the bore viewed as a metallic circular waveguide, enable traveling waves along the bore, and control the field in the bore and the phantom, e.g., dielectric rod arrays. In an approach that generated lots of interest, a traveling wave antenna was used, and it was shown that RF signals could reach organs located quite far away from the antenna itself; however, the main issue with traveling wave MRI is very low RF power efficiency. The state-of-the-art traveling wave antennas as implemented at $B_0 \geq 7$ T include circular- or square-shaped patch antennas that excite linear or CP fields inside a scanner's bore. This excitation, however, if not aided by additional electrodynamic elements (dielectrics or metamaterials), is highly localized, which results in rapid power dissipation in the body and thus in high local SAR levels in regions of the body and quick attenuation with distance away from the antenna. An example of RF volume coils is a subject-loaded multifilar (multichannel) helical-antenna inner-volume coil, which exploits both near-field and far-field regimes. In addition, breakthrough solutions for UHF were demonstrated with the advent of RF coil arrays, based on loop, stripline or dipole elements, fed with multi-channel RF technology such as $B_1$ shimming and transmit SENSE, triggering a large number of coil element designs to be compared. Overall, RF coil design for human UHF scanners remains an area of intense development, and especially regarding the most challenging targets, e.g., those requiring torso RF excitation, also known as "body imaging" With none of the outlined concepts, methods, and designs, and with no other concept, method, or design that is available in literature, are the principal desired objectives for the UHF RF excitation outlined above met to a satisfactory extent.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Use of the phrase "and/or" indicates that anyone or any combination of a list of options can be used. For example, "A, B, and/or C" means "A", or "B", or "C", or "A and B", or "A and C", or "B and C", or "A and B and C". As used in the specification, the singular forms "a," "an" and "the" include plural referents unless the context clearly dictates otherwise. Moreover, titles or subtitles may be used in this specification for the convenience of a reader, which shall have no influence on the scope of the disclosed technology. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose.

It is to be understood that the mention of one or more steps of a method does not preclude the presence of additional method steps or intervening method steps between those steps expressly identified. Steps of a method may be performed in a different order than those described herein. Similarly, it is also to be understood that the mention of one or more components in a device or system does not preclude the presence of additional components or intervening components between those components expressly identified.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, and at the end thereof, various publications are referenced. The disclosures of these publications in their entireties are hereby incorporated by reference into this application in order to more fully describe the state of the art to which the methods and systems pertain.

What is claimed is:

1. A magnetic resonance (MR) radiofrequency (RF) coil comprising:
    a plurality of slotted waveguides that collectively form an array circumferentially positioned about a longitudinal axis defining a bore scanning region of a magnetic resonance scanning system, each of the plurality of slotted waveguides having a unitary elongated body that extends parallel with, and along a pre-defined length of, the longitudinal axis, the unitary elongated body of each of the plurality of slotted waveguides defined by a set of walls that further define an interior space, the unitary elongated body of each of the plurality of slotted waveguides further comprising:
        an inner-facing surface that faces the longitudinal axis;
        a first side surface that extends from the inner-facing surface;
        a second side surface that extends from the inner-facing surface opposite that of the first side surface;
        a plurality of slotted openings, including a first slotted opening and a second slotted opening, each intermittently formed on the inner-facing surface and along a portion of the pre-defined length to introduce discontinuities in the elongated body and interrupt a flow of surface electric current along the inner-facing surface to flow to the first side surface and to the second side surface, wherein each of the plurality of slotted openings extends from the inner-facing surface to the interior space of the respective unitary elongated body, wherein the first slotted opening is formed at a first position on the inner-facing surface and the second slotted opening is formed at a second position on the inner-facing surface that is different from the first position, wherein the second position is a distance of $\lambda_g/2$ from the first position along a longitudinal axis of the unitary elongated body, wherein $\lambda_g$ is a guided wavelength in at least one of the plurality of slotted waveguide; and
        a dielectric lens for smoothing an impedance transition from the plurality of slotted openings to free space and reducing backpropagation, wherein the dielectric lens is in contact with the inner-facing surface and extends outward from the inner-facing surface, and wherein a portion of the dielectric lens extends over the first side surface and the second side surface.

2. The MR RF coil of claim 1, wherein the unitary elongated body at the first slotted opening is configured to act as a dipole antenna in generating a polarization from the interrupted flow of surface electric current along the inner-facing surface to the first and second side surface.

3. The MR RF coil of claim 1, wherein the plurality of slotted openings have a shape selected from the group consisting of rectangles, parallelograms, circles, or ovals.

4. The MR-RF coil of claim 1, wherein the plurality of slotted openings are formed in at least two rows extending in parallel along the pre-defined length of the unitary elongated body.

5. The MR RF coil of claim 4, wherein a subset of the plurality of slotted openings forming a first row of the at least two rows are offset longitudinally from a subset of the plurality of slotted openings forming a second row of the at least two rows.

6. The MR RF coil of claim 1, wherein a spacing between each of the plurality of slotted openings and the first and second side surfaces, including between the first and second side surfaces and the first slotted opening, and the first and second side surfaces and the second slotted opening, is non-uniform.

7. The MR RF coil of claim 1, wherein the unitary elongated body of each of the plurality of slotted waveguides has an outer cross-sectional profile selected from the group consisting of a rectangle, a square, a circle, and an oval.

8. The MR RF coil of claim 1, wherein the unitary elongated body of each of the plurality of slotted waveguides is hollow.

9. The MR RF coil of claim 1, wherein each of the plurality of slotted waveguides terminates at a short-circuit element or at a matched load element.

10. The MR RF coil of claim 1, wherein the plurality of slotted waveguides comprises between 3 and 24 slotted waveguides.

11. The MR RF coil of claim 1 further comprising one or more dielectric lenses held in at least partial contact with the inner-facing surface of the unitary elongated body of each of the plurality of slotted waveguides.

12. The MR RF coil of claim 1, wherein the plurality of slotted waveguides are configured for a magnetic field greater than 3 T.

13. The MR RF coil of claim 1, wherein the array is configured as one of the groups of a body coil, a head coil, a limb coil, and a torso coil.

14. The MR RF coil of claim 1, wherein the plurality of slotted openings includes the first slotted opening, the second slotted opening, and at least two additional slotted openings, wherein a positioning between the plurality of slotted openings is tapered towards the ends of the unitary elongated body.

15. The MR RF coil of claim 1, wherein a geometry of each of the plurality of slotted openings is non-uniform.

16. The MR RF coil of claim 1, wherein the first slotted opening is located a first distance from an end of the unitary elongated body, wherein the second slotted opening is located a second distance from the first slotted opening, wherein the first distance and the second distance are different.

17. The MR RF coil of claim 1, wherein the first slotted opening is located a third distance from at least one of the first side surface or the second side surface of the unitary elongated body, wherein the second slotted opening is located a fourth distance from the first slotted opening, wherein the third distance and the fourth distance are different.

18. The MR RF coil of claim 1, wherein the unitary elongated body of each of the plurality of slotted waveguides is filled with a dielectric, the pre-defined length of the unitary elongated body being defined by the dielectric.

19. The MR RF coil of claim 1, wherein the plurality of slotted openings further cause the electromagnetic field to radiate to an exterior of a respective unitary elongated body.

20. A magnetic resonance (MR) scanning system comprising:
a structure defining a bore within which a subject is to be positioned for scanning, the bore defining a longitudinal axis;
a magnet to generate a primary magnetic field within the bore parallel to the longitudinal axis;
a radiofrequency (RF) antennae coil comprising a plurality of slotted waveguides that collectively form an array circumferentially positioned about the longitudinal axis, each of the plurality of slotted waveguides having a unitary elongated body that extends parallel with, and along a pre-defined length of, the longitudinal axis, the unitary elongated body of each of the plurality of slotted waveguides defined by a set of walls that further define an interior space, the unitary elongated body of each of the plurality of slotted waveguides further comprising:
an inner surface that faces the longitudinal axis;
a first side surface that extends from the inner surface;
a second side surface that extends from the inner surface opposite that of the first side surface;
a plurality of slotted openings each intermittently formed on the inner surface and along a portion of the pre-defined length, to introduce discontinuities in the unitary elongated body and interrupt a flow of surface electric current along the inner surface to flow to the first side surface and to the second side surface, wherein each of the plurality of slotted openings extends from the inner surface to the interior space of the respective unitary elongated body, the plurality of slotted openings including a first opening and a second opening, wherein the first opening is formed at a first position and the second opening is formed at a second position that is different from the first position, wherein the second position is a distance of $\lambda_g/2$ from the first position along a longitudinal axis of the unitary elongated body, wherein $\lambda_g$ is a guided wavelength in at least one of the plurality of slotted waveguides; and
a dielectric lens for smoothing an impedance transition from the plurality of slotted openings to free space and reducing backpropagation, wherein the dielectric lens is in contact with the inner surface and extends outward from the inner surface, and wherein a portion of the dielectric lens extends over the first side surface and the second side surface;
a radiofrequency (RF) signal generator to drive the RF antennae coil to generate a circularly polarized (CP) RF magnetic field perpendicular to the longitudinal axis;
an RF detector to detect a response signal generated by tissues of the subject in response to the CP RF magnetic field; and
a computing system to create an image of the tissues of the subject based on the detected response signal.

21. The MR scanning system of claim 20, wherein the plurality of slotted openings of each of the plurality of slotted waveguides are selected from the group consisting of rectangles, parallelograms, circles, or ovals.

22. The MR scanning system of claim 20, wherein the plurality of slotted openings are formed in at least two rows on the inner surface of each of the plurality of slotted waveguides, wherein a first subset of the plurality of slotted openings form a first row of the at least two rows and are offset longitudinally from a second subset of the plurality of slotted openings that form a second row of the at least two rows.

* * * * *